US012807960B2

(12) United States Patent
Kubo et al.

(10) Patent No.: US 12,807,960 B2

(45) Date of Patent: Nov. 24, 2026

(54) TRANSFORMANT AND METHOD FOR PRODUCING CAROTENOID COMPOSITION USING SAME

(71) Applicant: EZAKI GLICO CO., LTD., Osaka (JP)

(72) Inventors: Akiko Kubo, Osaka (JP); Kohji Ohdan, Osaka (JP); Yoshinobu Terada, Osaka (JP); Katsuro Yaoi, Tsukuba (JP); Maiko Furubayashi, Sapporo (JP); Norihiko Misawa, Nonoichi (JP); Miho Kobayashi, Nonoichi (JP); Junichiro Hattan, Nonoichi (JP); Takashi Maoka, Kouka (JP)

(73) Assignee: EZAKI GLICO CO., LTD., Osaka (JP)

( * ) Notice: Subject to any disclaimer, the term of this patent is extended or adjusted under 35 U.S.C. 154(b) by 725 days.

(21) Appl. No.: 18/036,611

(22) PCT Filed: Nov. 9, 2021

(86) PCT No.: PCT/JP2021/041098

§ 371 (c)(1),
(2) Date: May 11, 2023

(87) PCT Pub. No.: WO2022/102595

PCT Pub. Date: May 19, 2022

(65) Prior Publication Data

US 2023/0416759 A1 Dec. 28, 2023

(30) Foreign Application Priority Data

Nov. 12, 2020 (JP) ................................ 2020-188462

(51) Int. Cl.

| | |
|---|---|
| ***C12N 15/52*** | (2006.01) |
| ***C12N 5/10*** | (2006.01) |
| ***C12N 9/02*** | (2006.01) |
| ***C12N 9/10*** | (2006.01) |
| ***C12N 15/70*** | (2006.01) |

(52) U.S. Cl.

CPC .............. *C12N 15/52* (2013.01); *C12N 5/10* (2013.01); *C12N 9/001* (2013.01); *C12N 9/1085* (2013.01); *C12N 15/70* (2013.01); *C12Y 103/99031* (2013.01); *C12Y 205/01029* (2013.01); *C12Y 205/01032* (2013.01)

(58) Field of Classification Search

CPC ...................................................... C12N 15/52

See application file for complete search history.

(56) References Cited

U.S. PATENT DOCUMENTS

| | | |
|---|---|---|
| 5,880,332 A | 3/1999 | Camara et al. |
| 8,592,662 B2 | 11/2013 | Todd, Jr. et al. |
| 9,247,694 B2 | 2/2016 | Todd, Jr. et al. |
| 10,721,946 B2 | 7/2020 | Todd, Jr. et al. |
| 2006/0182826 A1 | 8/2006 | Barren et al. |
| 2006/0185034 A1 | 8/2006 | Todd, Jr. et al. |
| 2011/0258744 A1 | 10/2011 | Todd, Jr. et al. |
| 2012/0216321 A1 | 8/2012 | Todd, Jr. et al. |
| 2014/0086986 A1 | 3/2014 | Todd, Jr. et al. |
| 2014/0380516 A1 | 12/2014 | Bruan, III et al. |
| 2016/0143329 A1 | 5/2016 | Todd, Jr. et al. |

FOREIGN PATENT DOCUMENTS

| | | |
|---|---|---|
| JP | H09-510608 A | 10/1997 |
| JP | 2008-532492 | 8/2008 |
| KR | 101424123 B1 | 8/2014 |

OTHER PUBLICATIONS

Extended European Search Report for App. No. 21891841.5 dated Jan. 7, 2025 in 9 pages.

Misawa, Norihiko, "Construction of an efficient system for the production of red pepper carotenoids and new derivatives", *Noda Institute for Scientific Research GRANT 2013 Research Grant*, (2013) pp. 43-44.

Takemura, Miho et al., "Pathway engineering for efficient biosynthesis of violaxanthinin *Escherichia coli", Applied Microbiology and Biotechnology* (2019) 103:9393-9399.

International Search Report received in International Application No. PCT/JP2021/041098, mailed on Jan. 25, 2022, in 4 pages.

Takemura et al., "(6E) and (6Z)-9'-Aporhodoxanthinone, novel carotenoids produced in zeaxanthin-synthesizing-*Escherichia coli* by redox stress". Tetrahedron Letters 56 (2015) pp. 6063-6065.

Kakinuma et al., "New Approach to Multiply Deuterated Isoprenoids Using Triply Engineered *Escherichia coli* and Its Potential as a Tool for Mechanistic Enzymology". J. Am. Chem. Soc., vol. 123, No. 6, 2001. American Chemical Society. pp. 1238-1239.

Furubayashi et al., "Capsanthin Production in *Escherichia coli* by Overexpression of Capsanthin/Capsorubin Synthase from Capsicum annuum". Journal of Agricultural and Food Chemistry. Apr. 23, 2021, 69, pp. 5076-5085.

Jeknic et al., Cloning and Functional Characterization of a Gene for Capsanthin-Capsorubin Synthase from Tiger Lily (*Lilium lancifolium* Thunb. 'Splendens'). Plant and Cell Physiology, vol. 53, Issue 11, Nov. 2012, 53(11), pp. 1899-1912.

Kumagai, et al., "Functional integration of non-native carotenoids into chloroplasts by viral-derived expression of capsantin-capsorubin synthase in *Nicotiana benthamiana*". The Plant Journal. 1998, 14(3), pp. 305-315.

(Continued)

*Primary Examiner* — Suzanne M Noakes

(74) *Attorney, Agent, or Firm* — Knobbe, Martens, Olson & Bear, LLP

(57) ABSTRACT

The present invention provides a technique for synthesizing a carotenoid composition by a genetic recombination technique. A transformant in which a first promoter, an upstream gene of a carotenoid biosynthesis gene including a crtY and crtZ operably linked to the first promoter, a second promoter having higher promoter intensity than the first promoter, and a ZEP gene and a CCS gene operably linked to the second promoter have been introduced into a host cell.

13 Claims, 8 Drawing Sheets

Specification includes a Sequence Listing.

(56) References Cited

OTHER PUBLICATIONS

Bouvier et al., "Xanthophyll biosynthesis in chromoplasts; isolation and molecular cloning of an enzyme catalyzing the conversion of 5,6-epoxycarotenoid into ketocarotenoid". The Plant Journal (1994), 6(1), pp. 45-54.
Rohmer et al., "Isoprenoid biosynthesis in bacteria: a novel pathway for the early steps leading to isopentenyl diphosphate". Biochem. J. (1993) 295: 517-524.
Kajiwara et al., "Expression of an exogenous isopentenyl diphosphate isomerase gene enhances isoprenoid biosynthesis in *Esherichia coli*". Biochem. J. (1997) 324: 421-426.
Lempens et al., "Noncovalent Synthesis of Protein Dendrimers", Chemistry, A European Journal, (2009) 15: 8760-8767.
Harada et al "Carotenoid production by recombinant microorganisms: Current status and prospects of carotenoid research and development" Journal of the Society for Biotechnology, Japan, vol. 93(7): 397.

DMAPP
GPP
FPP
IPP
GGPP
Phytoene
Lycopene
β-Carotene
β-Cryptoxanthin
Zeaxanthin
Antheraxanthin
Violaxanthin
Cucurbitaxanthin A
Capsanthin 3,6-epoxide 3'-acetate
Capsanthin 3,6-epoxide
Capsanthin 3'-acetate
Capsanthin
Capsorubin
Capsorubin 3-acetate
Capsorubin diacetate Comparative Example 1

1 Violaxanthin
3 Zeaxanthin
2 Antheraxanthin
4 β-carotene
Capsanthin

1 Violaxanthin

3 Zeaxanthin

2 Antheraxanthin

4 β-carotene

5 Capsanthin

Example 3-1 Example 3-2 Example 3-3

SEQUENCE LISTING

```
<160> NUMBER OF SEQ ID NOS: 12

<210> SEQ ID NO 1
<211> LENGTH: 321
<212> TYPE: DNA
<213> ORGANISM: Homo sapiens

<400> SEQUENCE: 1

atggattcta gctcaaacta ttgtaatcaa atgatgaaat cccgtaacct gaccaaagac     60

cgctgtaaac ctgtcaatac ctttgtccac gaatctttag ccgatgttca agccgtgtgt    120

tctcaaaaaa atgtagcctg taaaaatggc caaaccaact gttatcaatc atattccacc    180

atgtccatta ccgattgtcg cgaaacagga tcttccaaat atccaaattg tgcatataaa    240

actacccaag cgaacaaaca tattatcgta gcatgtgaag gcaacccgta cgtacctgtc    300

cacttcgacg catcagtgta a                                              321


<210> SEQ ID NO 2
<211> LENGTH: 106
<212> TYPE: PRT
<213> ORGANISM: Homo sapiens

<400> SEQUENCE: 2

Met Asp Ser Ser Ser Asn Tyr Cys Asn Gln Met Met Lys Ser Arg Asn
```

-continued

```
1               5                   10                  15

Leu Thr Lys Asp Arg Cys Lys Pro Val Asn Thr Phe Val His Glu Ser
            20                  25                  30

Leu Ala Asp Val Gln Ala Val Cys Ser Gln Lys Asn Val Ala Cys Lys
        35                  40                  45

Asn Gly Gln Thr Asn Cys Tyr Gln Ser Tyr Ser Thr Met Ser Ile Thr
    50                  55                  60

Asp Cys Arg Glu Thr Gly Ser Ser Lys Tyr Pro Asn Cys Ala Tyr Lys
65                  70                  75                  80

Thr Thr Gln Ala Asn Lys His Ile Ile Val Ala Cys Glu Gly Asn Pro
                85                  90                  95

Tyr Val Pro Val His Phe Asp Ala Ser Val
            100                 105


<210> SEQ ID NO 3
<211> LENGTH: 60
<212> TYPE: DNA
<213> ORGANISM: Artificial Sequence
<220> FEATURE:
<223> OTHER INFORMATION: S-Tag coding oligonucloetide with substitution
      at 34th to 36th position by phenylalanine coding sequence

<400> SEQUENCE: 3

aaagaaaccg ctgctgcgaa atttgaacgc cagttcatgg actcgtctac tagcgcagct     60


<210> SEQ ID NO 4
<211> LENGTH: 20
<212> TYPE: PRT
<213> ORGANISM: Artificial Sequence
<220> FEATURE:
<223> OTHER INFORMATION: S-Tag amino sequence with substitution at 12th
      position by phenylalanine

<400> SEQUENCE: 4

Lys Glu Thr Ala Ala Ala Lys Phe Glu Arg Gln Phe Met Asp Ser Ser
1               5                   10                  15

Thr Ser Ala Ala
            20


<210> SEQ ID NO 5
<211> LENGTH: 1446
<212> TYPE: DNA
<213> ORGANISM: Artificial Sequence
<220> FEATURE:
<223> OTHER INFORMATION: S-Tag introduced CaCCS

<400> SEQUENCE: 5

atggcaaaag aaaccgctgc tgcgaaattt gaacgccagt tcatggactc gtctactagc     60

gcagctatgt ttcattatcg taacaaaagc agcacccatt tttgcagctt tctggatctg    120

gcgccgacca gcaaaccgga aagcctggat gtgaatatca gctgggttga taccgatctg    180

gatggcgccg aatttgatgt gattatcatt ggtaccggtc cggccggcct gcgtctggca    240

gaacaggtta gcaaatatgg tattaaagtg tgctgtgttg atccgagccc gctgagcatg    300

tggccgaaca attatggcgt gtgggttgat gaatttgaaa aactgggtct ggaagattgc    360

ctggatcata aatggccggt gagctgtgtt catatcagcg atcataaaac caaatatctg    420

gatcgcccgt atggtcgcgt gagccgtaaa aaactgaaac tgaaactgct gaacagctgc    480

gtggaaaacc gtgttaaatt ctacaaagcg aaagtgctga aagttaaaca tgaagaattt    540

gaaagcagca ttgtgtgtga tgatggccgc aaaatcagcg gtagcctgat tgttgatgcg    600
```

```
agcggctatg ccagcgattt tatcgaatat gataaaccgc gtaatcatgg ctatcaggtg    660

gcgcatggta ttctggccga agttgataat catccgtttg atctggataa aatgatgctg    720

atggattggc gcgatagcca tctgggtaac gaaccgtatc tgcgtgtgaa aaataccaaa    780

gaaccgacct ttctgtatgc gatgccgttt gatcgcaatc tggtgtttct ggaagaaacc    840

agcctggtta gccgtccgat gctgagctat atggaagtga aacgtcgcat ggttgcccgc    900

ctgcgtcatc tgggcattaa agtgcgcagc gttctggaag aagaaaaatg tgtgatcacg    960

atgggcggcc cgctgccgcg tattccgcag aacgttatgg cgatcggcgg taccagcggc   1020

attgtgcatc cgagcagcgg ttatatggtt gcgcgcagca tggcgctggc accggtgctg   1080

gcggaagcca tcgttgaaag cctgggcagc acccgcatga ttcgtggtag ccagctgtat   1140

catcgcgtgt ggaatggtct gtggccgagc gatcgtcgcc gtgttcgtga atgctattgt   1200

tttggcatgg aaaccttatt aaaactggat ctggaaggta cccgccgtct gtttgatgcg   1260

tttttcgatg ttgatccgaa atattggcat ggctttctga gcagccgcct gagcgtgaaa   1320

gaactggccg ttctgagcct gtacctgttt ggtcatgcga gcaacctggc ccgtctggat   1380

atcgtgacca aatgtaccgt gccgctggtt aaactgctgg gcaatctggc gattgaaagc   1440

ctgtaa                                                              1446
```

<210> SEQ ID NO 6
<211> LENGTH: 481
<212> TYPE: PRT
<213> ORGANISM: Artificial Sequence
<220> FEATURE:
<223> OTHER INFORMATION: S-Tag introduced CaCCS

<400> SEQUENCE: 6

```
Met Ala Lys Glu Thr Ala Ala Ala Lys Phe Glu Arg Gln Phe Met Asp
1               5                   10                  15

Ser Ser Thr Ser Ala Ala Met Phe His Tyr Arg Asn Lys Ser Ser Thr
            20                  25                  30

His Phe Cys Ser Phe Leu Asp Leu Ala Pro Thr Ser Lys Pro Glu Ser
        35                  40                  45

Leu Asp Val Asn Ile Ser Trp Val Asp Thr Asp Leu Asp Gly Ala Glu
    50                  55                  60

Phe Asp Val Ile Ile Ile Gly Thr Gly Pro Ala Gly Leu Arg Leu Ala
65                  70                  75                  80

Glu Gln Val Ser Lys Tyr Gly Ile Lys Val Cys Cys Val Asp Pro Ser
                85                  90                  95

Pro Leu Ser Met Trp Pro Asn Asn Tyr Gly Val Trp Val Asp Glu Phe
            100                 105                 110

Glu Lys Leu Gly Leu Glu Asp Cys Leu Asp His Lys Trp Pro Val Ser
        115                 120                 125

Cys Val His Ile Ser Asp His Lys Thr Lys Tyr Leu Asp Arg Pro Tyr
    130                 135                 140

Gly Arg Val Ser Arg Lys Lys Leu Lys Leu Lys Leu Leu Asn Ser Cys
145                 150                 155                 160

Val Glu Asn Arg Val Lys Phe Tyr Lys Ala Lys Val Leu Lys Val Lys
                165                 170                 175

His Glu Glu Phe Glu Ser Ser Ile Val Cys Asp Asp Gly Arg Lys Ile
            180                 185                 190

Ser Gly Ser Leu Ile Val Asp Ala Ser Gly Tyr Ala Ser Asp Phe Ile
        195                 200                 205
```

```
Glu Tyr Asp Lys Pro Arg Asn His Gly Tyr Gln Val Ala His Gly Ile
    210                 215                 220

Leu Ala Glu Val Asp Asn His Pro Phe Asp Leu Asp Lys Met Met Leu
225                 230                 235                 240

Met Asp Trp Arg Asp Ser His Leu Gly Asn Glu Pro Tyr Leu Arg Val
                245                 250                 255

Lys Asn Thr Lys Glu Pro Thr Phe Leu Tyr Ala Met Pro Phe Asp Arg
            260                 265                 270

Asn Leu Val Phe Leu Glu Glu Thr Ser Leu Val Ser Arg Pro Met Leu
        275                 280                 285

Ser Tyr Met Glu Val Lys Arg Arg Met Val Ala Arg Leu Arg His Leu
    290                 295                 300

Gly Ile Lys Val Arg Ser Val Leu Glu Glu Glu Lys Cys Val Ile Thr
305                 310                 315                 320

Met Gly Gly Pro Leu Pro Arg Ile Pro Gln Asn Val Met Ala Ile Gly
                325                 330                 335

Gly Thr Ser Gly Ile Val His Pro Ser Ser Gly Tyr Met Val Ala Arg
            340                 345                 350

Ser Met Ala Leu Ala Pro Val Leu Ala Glu Ala Ile Val Glu Ser Leu
        355                 360                 365

Gly Ser Thr Arg Met Ile Arg Gly Ser Gln Leu Tyr His Arg Val Trp
    370                 375                 380

Asn Gly Leu Trp Pro Ser Asp Arg Arg Arg Val Arg Glu Cys Tyr Cys
385                 390                 395                 400

Phe Gly Met Glu Thr Leu Leu Lys Leu Asp Leu Glu Gly Thr Arg Arg
                405                 410                 415

Leu Phe Asp Ala Phe Phe Asp Val Asp Pro Lys Tyr Trp His Gly Phe
            420                 425                 430

Leu Ser Ser Arg Leu Ser Val Lys Glu Leu Ala Val Leu Ser Leu Tyr
        435                 440                 445

Leu Phe Gly His Ala Ser Asn Leu Ala Arg Leu Asp Ile Val Thr Lys
    450                 455                 460

Cys Thr Val Pro Leu Val Lys Leu Leu Gly Asn Leu Ala Ile Glu Ser
465                 470                 475                 480

Leu
```

<210> SEQ ID NO 7
<211> LENGTH: 1506
<212> TYPE: DNA
<213> ORGANISM: Artificial Sequence
<220> FEATURE:
<223> OTHER INFORMATION: S-Tag introduced CaCCS via linker

<400> SEQUENCE: 7

```
atgtcgaaag aaaccgctgc tgcgaaattt gaacgccagt tcatggactc gtctactagt      60

gcagctggtt caggtagtgg ttcaggttct ggttcaggtt caggtagtgg ttcaggttct     120

ggttcaatgt ttcattatcg taacaaaagc agcacccatt tttgcagctt tctggatctg     180

gcgccgacca gcaaaccgga aagcctggat gtgaatatca gctgggttga taccgatctg     240

gatggcgccg aatttgatgt gattatcatt ggtaccggtc cggccggcct gcgtctggca     300

gaacaggtta gcaaatatgg tattaaagtg tgctgtgttg atccgagccc gctgagcatg     360

tggccgaaca attatggcgt gtgggttgat gaatttgaaa aactgggtct ggaagattgc     420

ctggatcata aatggccggt gagctgtgtt catatcagcg atcataaaac caaatatctg     480
```

```
gatcgcccgt atggtcgcgt gagccgtaaa aaactgaaac tgaaactgct gaacagctgc    540

gtggaaaacc gtgttaaatt ctacaaagcg aaagtgctga aagttaaaca tgaagaattt    600

gaaagcagca ttgtgtgtga tgatggccgc aaaatcagcg gtagcctgat tgttgatgcg    660

agcggctatg ccagcgattt tatcgaatat gataaaccgc gtaatcatgg ctatcaggtg    720

gcgcatggta ttctggccga agttgataat catccgtttg atctggataa aatgatgctg    780

atggattggc gcgatagcca tctgggtaac gaaccgtatc tgcgtgtgaa aaataccaaa    840

gaaccgacct ttctgtatgc gatgccgttt gatcgcaatc tggtgtttct ggaagaaacc    900

agcctggtta gccgtccgat gctgagctat atggaagtga aacgtcgcat ggttgcccgc    960

ctgcgtcatc tgggcattaa agtgcgcagc gttctggaag aagaaaaatg tgtgatcacg   1020

atgggcggcc cgctgccgcg tattccgcag aacgttatgg cgatcggcgg taccagcggc   1080

attgtgcatc cgagcagcgg ttatatggtt gcgcgcagca tggcgctggc accggtgctg   1140

gcggaagcca tcgttgaaag cctgggcagc acccgcatga ttcgtggtag ccagctgtat   1200

catcgcgtgt ggaatggtct gtggccgagc gatcgtcgcc gtgttcgtga atgctattgt   1260

tttggcatgg aaaccttatt aaaactggat ctggaaggta cccgccgtct gtttgatgcg   1320

tttttcgatg ttgatccgaa atattggcat ggctttctga gcagccgcct gagcgtgaaa   1380

gaactggccg ttctgagcct gtacctgttt ggtcatgcga gcaacctggc ccgtctggat   1440

atcgtgacca aatgtaccgt gccgctggtt aaactgctgg gcaatctggc gattgaaagc   1500

ctgtaa                                                              1506
```

<210> SEQ ID NO 8
<211> LENGTH: 501
<212> TYPE: PRT
<213> ORGANISM: Artificial Sequence
<220> FEATURE:
<223> OTHER INFORMATION: S-Tag introduced CaCCS via linker

<400> SEQUENCE: 8

```
Met Ser Lys Glu Thr Ala Ala Ala Lys Phe Glu Arg Gln Phe Met Asp
1               5                   10                  15

Ser Ser Thr Ser Ala Ala Gly Ser Gly Ser Gly Ser Gly Ser Gly Ser
            20                  25                  30

Gly Ser Gly Ser Gly Ser Gly Ser Gly Ser Met Phe His Tyr Arg Asn
        35                  40                  45

Lys Ser Ser Thr His Phe Cys Ser Phe Leu Asp Leu Ala Pro Thr Ser
    50                  55                  60

Lys Pro Glu Ser Leu Asp Val Asn Ile Ser Trp Val Asp Thr Asp Leu
65                  70                  75                  80

Asp Gly Ala Glu Phe Asp Val Ile Ile Ile Gly Thr Gly Pro Ala Gly
                85                  90                  95

Leu Arg Leu Ala Glu Gln Val Ser Lys Tyr Gly Ile Lys Val Cys Cys
            100                 105                 110

Val Asp Pro Ser Pro Leu Ser Met Trp Pro Asn Asn Tyr Gly Val Trp
        115                 120                 125

Val Asp Glu Phe Glu Lys Leu Gly Leu Glu Asp Cys Leu Asp His Lys
    130                 135                 140

Trp Pro Val Ser Cys Val His Ile Ser Asp His Lys Thr Lys Tyr Leu
145                 150                 155                 160

Asp Arg Pro Tyr Gly Arg Val Ser Arg Lys Lys Leu Lys Leu Lys Leu
                165                 170                 175
```

-continued

```
Leu Asn Ser Cys Val Glu Asn Arg Val Lys Phe Tyr Lys Ala Lys Val
            180                 185                 190

Leu Lys Val Lys His Glu Glu Phe Glu Ser Ser Ile Val Cys Asp Asp
        195                 200                 205

Gly Arg Lys Ile Ser Gly Ser Leu Ile Val Asp Ala Ser Gly Tyr Ala
    210                 215                 220

Ser Asp Phe Ile Glu Tyr Asp Lys Pro Arg Asn His Gly Tyr Gln Val
225                 230                 235                 240

Ala His Gly Ile Leu Ala Glu Val Asp Asn His Pro Phe Asp Leu Asp
                245                 250                 255

Lys Met Met Leu Met Asp Trp Arg Asp Ser His Leu Gly Asn Glu Pro
            260                 265                 270

Tyr Leu Arg Val Lys Asn Thr Lys Glu Pro Thr Phe Leu Tyr Ala Met
        275                 280                 285

Pro Phe Asp Arg Asn Leu Val Phe Leu Glu Glu Thr Ser Leu Val Ser
    290                 295                 300

Arg Pro Met Leu Ser Tyr Met Glu Val Lys Arg Arg Met Val Ala Arg
305                 310                 315                 320

Leu Arg His Leu Gly Ile Lys Val Arg Ser Val Leu Glu Glu Glu Lys
                325                 330                 335

Cys Val Ile Thr Met Gly Gly Pro Leu Pro Arg Ile Pro Gln Asn Val
            340                 345                 350

Met Ala Ile Gly Gly Thr Ser Gly Ile Val His Pro Ser Ser Gly Tyr
        355                 360                 365

Met Val Ala Arg Ser Met Ala Leu Ala Pro Val Leu Ala Glu Ala Ile
    370                 375                 380

Val Glu Ser Leu Gly Ser Thr Arg Met Ile Arg Gly Ser Gln Leu Tyr
385                 390                 395                 400

His Arg Val Trp Asn Gly Leu Trp Pro Ser Asp Arg Arg Arg Val Arg
                405                 410                 415

Glu Cys Tyr Cys Phe Gly Met Glu Thr Leu Leu Lys Leu Asp Leu Glu
            420                 425                 430

Gly Thr Arg Arg Leu Phe Asp Ala Phe Phe Asp Val Asp Pro Lys Tyr
        435                 440                 445

Trp His Gly Phe Leu Ser Ser Arg Leu Ser Val Lys Glu Leu Ala Val
    450                 455                 460

Leu Ser Leu Tyr Leu Phe Gly His Ala Ser Asn Leu Ala Arg Leu Asp
465                 470                 475                 480

Ile Val Thr Lys Cys Thr Val Pro Leu Val Lys Leu Leu Gly Asn Leu
                485                 490                 495

Ala Ile Glu Ser Leu
            500
```

<210> SEQ ID NO 9
<211> LENGTH: 2073
<212> TYPE: DNA
<213> ORGANISM: Artificial Sequence
<220> FEATURE:
<223> OTHER INFORMATION: S-Tag introduced CaZEP

<400> SEQUENCE: 9

```
atgtcgaaag aaaccgctgc tgcgaaattt gaacgccagt tcatggactc gtctactagt      60

gcagctatga ccatgattac gaattcgatg tatagcaccg tgttttatac cagcgttcat     120

ccgagcacca gcgtgtttag ccgcaaacag ctgccgctgc tgattagcaa agattttccg     180
```

-continued

```
gccgaactgt atcatagcct gccgtgcaaa agcctggaaa atggtcatat taagaaagtg    240
aaaggcgtta aagccaccct ggccgaagca ccggccaccc cgaccgaaaa atctaacagc    300
gaagtgccgc agaaaaaact gaaagtgctg gttgccggcg gtggcattgg tggcctggtg    360
tttgcgctgg cggcgaaaaa gaaaggcttt gatgtgctgg tttttgaacg tgatctgagc    420
gccatccgcg gcgaaggcca gtatcgtggc ccgattcaga tccagagcaa tgccctggcg    480
gccctggaag cgattgatat ggatgtggcc gaagaaatca tgaacgcggg ttgcattacc    540
ggccagcgta tcaatggtct ggttgatggt attagcggca actggtattg taaatttgat    600
acctttaccc cggccgtgga acgcggcctg ccggtgaccc gtgttattag ccgcatgacc    660
ctgcagcaga tcctggcacg tgccgtgggt gaagatgtta ttatgaacga aagcaatgtg    720
gttaactttg aagatgatgg cgaaaaagtg accgtggttc tggaaaatgg tcagcgcttt    780
accggcgatc tgctggttgg tgccgatggc atccgtagca aagtgcgcac caacctgttt    840
ggtcatagcg aagcgaccta tagcggttat acctgttata ccggcattgc cgattttgtt    900
ccggcggata tcgataccgt gggttatcgt gtttttctgg gccataaaca gtattttgtg    960
agcagcgatg ttggtggcgg taaaatgcag tggtatgcgt ttcataatga accggccggc   1020
ggtgtggatg ccccgaatgg caagaaagaa cgcctgctga aatttttggg cggttggtgc   1080
gataatgtga tcgatctgct ggttgccacc gatgaagatg cgattctgcg tcgcgatatc   1140
tatgatcgtc cgccgacctt taattggggt cgtggtcgtg tgaccctgct gggtgatagc   1200
gttcatgcca tgcagccgaa cctgggtcag ggcggttgta tggccattga agatagctat   1260
cagctggcgc tggaactgga aaaagcctgg agccgcagcg ccgaaagcgg tagcccgatg   1320
gatgttatca gcagcctgcg tagctatgaa agcgcccgta aactgcgcgt gggtgttatt   1380
catggcctgg cccgtatggc cgcaatcatg gcaagcacct ataaagcgta tctgggcgtg   1440
ggtctgggtc cgctgagctt tctgaccaaa tatcgtattc cgcacccggg tcgtgttggc   1500
ggtcgtgtgt ttgttgatct gggcatgccg ctgatgctga gctgggtgct gggcggtaat   1560
ggtgataaac tggaaggccg tatccagcat tgccgcctga gcgaaaaagc caacgatcag   1620
ctgcgtcgct ggtttgaaga tgatgatgcg ctggaacgcg ccaccgatgc cgaatggctg   1680
ctgctgccgg ccgcaaatgg caatagcgcg ctggaaacca ttgtgctgag ccgtgatgaa   1740
gatgttccgt gcaccattgg tagcgtgagc cataccaaca tcccgggcaa aagcgtggtt   1800
ctgccgctgc cgcaggttag cgaaatgcat gcccagatta gctgtaaaaa caatgcgttt   1860
ttcgtgaccg attttcagag cgaacatggt acctgggtta tcgataatga aggccgtcgc   1920
tatcgcgtga gcccgaactt tccgatgcgt tttcatagca gcgatgtgat tgtttttggt   1980
agcgataaag cggcctttcg cgtgaaaacc atgaaatttc cgagcaaaac cgccgaagcg   2040
aaagaagaac gtaaagtggt tggcaccgcg taa                                2073
```

<210> SEQ ID NO 10
<211> LENGTH: 690
<212> TYPE: PRT
<213> ORGANISM: Artificial Sequence
<220> FEATURE:
<223> OTHER INFORMATION: S-Tag introduced CaZEP

<400> SEQUENCE: 10

```
Met Ser Lys Glu Thr Ala Ala Ala Lys Phe Glu Arg Gln Phe Met Asp
1               5                   10                  15

Ser Ser Thr Ser Ala Ala Met Thr Met Ile Thr Asn Ser Met Tyr Ser
```

-continued

```
                20                  25                  30

Thr Val Phe Tyr Thr Ser Val His Pro Ser Thr Ser Val Phe Ser Arg
        35                  40                  45

Lys Gln Leu Pro Leu Leu Ile Ser Lys Asp Phe Pro Ala Glu Leu Tyr
    50                  55                  60

His Ser Leu Pro Cys Lys Ser Leu Glu Asn Gly His Ile Lys Lys Val
65                  70                  75                  80

Lys Gly Val Lys Ala Thr Leu Ala Glu Ala Pro Ala Thr Pro Thr Glu
                85                  90                  95

Lys Ser Asn Ser Glu Val Pro Gln Lys Lys Leu Lys Val Leu Val Ala
            100                 105                 110

Gly Gly Gly Ile Gly Gly Leu Val Phe Ala Leu Ala Ala Lys Lys Lys
        115                 120                 125

Gly Phe Asp Val Leu Val Phe Glu Arg Asp Leu Ser Ala Ile Arg Gly
    130                 135                 140

Glu Gly Gln Tyr Arg Gly Pro Ile Gln Ile Gln Ser Asn Ala Leu Ala
145                 150                 155                 160

Ala Leu Glu Ala Ile Asp Met Asp Val Ala Glu Glu Ile Met Asn Ala
                165                 170                 175

Gly Cys Ile Thr Gly Gln Arg Ile Asn Gly Leu Val Asp Gly Ile Ser
            180                 185                 190

Gly Asn Trp Tyr Cys Lys Phe Asp Thr Phe Thr Pro Ala Val Glu Arg
        195                 200                 205

Gly Leu Pro Val Thr Arg Val Ile Ser Arg Met Thr Leu Gln Gln Ile
    210                 215                 220

Leu Ala Arg Ala Val Gly Glu Asp Val Ile Met Asn Glu Ser Asn Val
225                 230                 235                 240

Val Asn Phe Glu Asp Asp Gly Glu Lys Val Thr Val Val Leu Glu Asn
                245                 250                 255

Gly Gln Arg Phe Thr Gly Asp Leu Leu Val Gly Ala Asp Gly Ile Arg
            260                 265                 270

Ser Lys Val Arg Thr Asn Leu Phe Gly His Ser Glu Ala Thr Tyr Ser
        275                 280                 285

Gly Tyr Thr Cys Tyr Thr Gly Ile Ala Asp Phe Val Pro Ala Asp Ile
    290                 295                 300

Asp Thr Val Gly Tyr Arg Val Phe Leu Gly His Lys Gln Tyr Phe Val
305                 310                 315                 320

Ser Ser Asp Val Gly Gly Gly Lys Met Gln Trp Tyr Ala Phe His Asn
                325                 330                 335

Glu Pro Ala Gly Gly Val Asp Ala Pro Asn Gly Lys Lys Glu Arg Leu
            340                 345                 350

Leu Lys Ile Phe Gly Gly Trp Cys Asp Asn Val Ile Asp Leu Leu Val
        355                 360                 365

Ala Thr Asp Glu Asp Ala Ile Leu Arg Arg Asp Ile Tyr Asp Arg Pro
    370                 375                 380

Pro Thr Phe Asn Trp Gly Arg Gly Arg Val Thr Leu Leu Gly Asp Ser
385                 390                 395                 400

Val His Ala Met Gln Pro Asn Leu Gly Gln Gly Gly Cys Met Ala Ile
                405                 410                 415

Glu Asp Ser Tyr Gln Leu Ala Leu Glu Leu Glu Lys Ala Trp Ser Arg
            420                 425                 430

Ser Ala Glu Ser Gly Ser Pro Met Asp Val Ile Ser Ser Leu Arg Ser
        435                 440                 445
```

-continued

Tyr Glu Ser Ala Arg Lys Leu Arg Val Gly Val Ile His Gly Leu Ala
    450                 455                 460

Arg Met Ala Ala Ile Met Ala Ser Thr Tyr Lys Ala Tyr Leu Gly Val
465                 470                 475                 480

Gly Leu Gly Pro Leu Ser Phe Leu Thr Lys Tyr Arg Ile Pro His Pro
                485                 490                 495

Gly Arg Val Gly Gly Arg Val Phe Val Asp Leu Gly Met Pro Leu Met
            500                 505                 510

Leu Ser Trp Val Leu Gly Gly Asn Gly Asp Lys Leu Glu Gly Arg Ile
        515                 520                 525

Gln His Cys Arg Leu Ser Glu Lys Ala Asn Asp Gln Leu Arg Arg Trp
    530                 535                 540

Phe Glu Asp Asp Asp Ala Leu Glu Arg Ala Thr Asp Ala Glu Trp Leu
545                 550                 555                 560

Leu Leu Pro Ala Ala Asn Gly Asn Ser Ala Leu Glu Thr Ile Val Leu
                565                 570                 575

Ser Arg Asp Glu Asp Val Pro Cys Thr Ile Gly Ser Val Ser His Thr
            580                 585                 590

Asn Ile Pro Gly Lys Ser Val Val Leu Pro Leu Pro Gln Val Ser Glu
        595                 600                 605

Met His Ala Gln Ile Ser Cys Lys Asn Asn Ala Phe Phe Val Thr Asp
    610                 615                 620

Phe Gln Ser Glu His Gly Thr Trp Val Ile Asp Asn Glu Gly Arg Arg
625                 630                 635                 640

Tyr Arg Val Ser Pro Asn Phe Pro Met Arg Phe His Ser Ser Asp Val
                645                 650                 655

Ile Val Phe Gly Ser Asp Lys Ala Ala Phe Arg Val Lys Thr Met Lys
            660                 665                 670

Phe Pro Ser Lys Thr Ala Glu Ala Lys Glu Glu Arg Lys Val Val Gly
        675                 680                 685

Thr Ala
    690

<210> SEQ ID NO 11
<211> LENGTH: 2133
<212> TYPE: DNA
<213> ORGANISM: Artificial Sequence
<220> FEATURE:
<223> OTHER INFORMATION: S-Tag introduced CaZEP via linker

<400> SEQUENCE: 11
atgtcgaaag aaaccgctgc tgcgaaattt gaacgccagt tcatggactc gtctactagt 60
gcagctggtt caggtagtgg ttcaggttct ggttcaggtt caggtagtgg ttcaggttct 120
ggttcaatga ccatgattac gaattcgatg tatagcaccg tgttttatac cagcgttcat 180
ccgagcacca gcgtgtttag ccgcaaacag ctgccgctgc tgattagcaa agattttccg 240
gccgaactgt atcatagcct gccgtgcaaa agcctggaaa atggtcatat taagaaagtg 300
aaaggcgtta aagccaccct ggccgaagca ccggccaccc cgaccgaaaa atctaacagc 360
gaagtgccgc agaaaaaact gaaagtgctg gttgccggcg gtggcattgg tggcctggtg 420
tttgcgctgg cggcgaaaaa gaaaggcttt gatgtgctgg tttttgaacg tgatctgagc 480
gccatccgcg gcgaaggcca gtatcgtggc ccgattcaga tccagagcaa tgccctggcg 540
gccctggaag cgattgatat ggatgtggcc gaagaaatca tgaacgcggg ttgcattacc 600

-continued

```
ggccagcgta tcaatggtct ggttgatggt attagcggca actggtattg taaatttgat    660

acctttaccc cggccgtgga acgcggcctg ccggtgaccc gtgttattag ccgcatgacc    720

ctgcagcaga tcctggcacg tgccgtgggt gaagatgtta ttatgaacga aagcaatgtg    780

gttaactttg aagatgatgg cgaaaaagtg accgtggttc tggaaaatgg tcagcgcttt    840

accggcgatc tgctggttgg tgccgatggc atccgtagca aagtgcgcac caacctgttt    900

ggtcatagcg aagcgaccta tagcggttat acctgttata ccggcattgc cgattttgtt    960

ccggcggata tcgataccgt gggttatcgt gtttttctgg gccataaaca gtattttgtg   1020

agcagcgatg ttggtggcgg taaaatgcag tggtatgcgt ttcataatga accggccggc   1080

ggtgtggatg ccccgaatgg caagaaagaa cgcctgctga aatttttgg cggttggtgc    1140

gataatgtga tcgatctgct ggttgccacc gatgaagatg cgattctgcg tcgcgatatc   1200

tatgatcgtc cgccgacctt taattggggt cgtggtcgtg tgaccctgct gggtgatagc   1260

gttcatgcca tgcagccgaa cctgggtcag ggcggttgta tggccattga agatagctat   1320

cagctggcgc tggaactgga aaaagcctgg agccgcagcg ccgaaagcgg tagcccgatg   1380

gatgttatca gcagcctgcg tagctatgaa agcgcccgta aactgcgcgt gggtgttatt   1440

catggcctgg cccgtatggc cgcaatcatg gcaagcacct ataaagcgta tctgggcgtg   1500

ggtctgggtc cgctgagctt tctgaccaaa tatcgtattc cgcacccggg tcgtgttggc   1560

ggtcgtgtgt ttgttgatct gggcatgccg ctgatgctga gctgggtgct gggcggtaat   1620

ggtgataaac tggaaggccg tatccagcat tgccgcctga gcgaaaaagc caacgatcag   1680

ctgcgtcgct ggtttgaaga tgatgatgcg ctggaacgcg ccaccgatgc cgaatggctg   1740

ctgctgccgg ccgcaaatgg caatagcgcg ctggaaacca ttgtgctgag ccgtgatgaa   1800

gatgttccgt gcaccattgg tagcgtgagc cataccaaca tcccgggcaa aagcgtggtt   1860

ctgccgctgc cgcaggttag cgaaatgcat gcccagatta gctgtaaaaa caatgcgttt   1920

ttcgtgaccg attttcagag cgaacatggt acctgggtta tcgataatga aggccgtcgc   1980

tatcgcgtga gcccgaactt tccgatgcgt tttcatagca gcgatgtgat tgtttttggt   2040

agcgataaag cggcctttcg cgtgaaaacc atgaaatttc cgagcaaaac cgccgaagcg   2100

aaagaagaac gtaaagtggt tggcaccgcg taa                                 2133
```

<210> SEQ ID NO 12
<211> LENGTH: 710
<212> TYPE: PRT
<213> ORGANISM: Artificial Sequence
<220> FEATURE:
<223> OTHER INFORMATION: S-Tag introduced CaZEP via linker

<400> SEQUENCE: 12

```
Met Ser Lys Glu Thr Ala Ala Ala Lys Phe Glu Arg Gln Phe Met Asp
1               5                   10                  15

Ser Ser Thr Ser Ala Ala Gly Ser Gly Ser Gly Ser Gly Ser Gly Ser
            20                  25                  30

Gly Ser Gly Ser Gly Ser Gly Ser Gly Ser Met Thr Met Ile Thr Asn
        35                  40                  45

Ser Met Tyr Ser Thr Val Phe Tyr Thr Ser Val His Pro Ser Thr Ser
    50                  55                  60

Val Phe Ser Arg Lys Gln Leu Pro Leu Leu Ile Ser Lys Asp Phe Pro
65                  70                  75                  80

Ala Glu Leu Tyr His Ser Leu Pro Cys Lys Ser Leu Glu Asn Gly His
                85                  90                  95
```

-continued

```
Ile Lys Lys Val Lys Gly Val Lys Ala Thr Leu Ala Glu Ala Pro Ala
            100                 105                 110

Thr Pro Thr Glu Lys Ser Asn Ser Glu Val Pro Gln Lys Lys Leu Lys
        115                 120                 125

Val Leu Val Ala Gly Gly Gly Ile Gly Gly Leu Val Phe Ala Leu Ala
    130                 135                 140

Ala Lys Lys Lys Gly Phe Asp Val Leu Val Phe Glu Arg Asp Leu Ser
145                 150                 155                 160

Ala Ile Arg Gly Glu Gly Gln Tyr Arg Gly Pro Ile Gln Ile Gln Ser
                165                 170                 175

Asn Ala Leu Ala Ala Leu Glu Ala Ile Asp Met Asp Val Ala Glu Glu
            180                 185                 190

Ile Met Asn Ala Gly Cys Ile Thr Gly Gln Arg Ile Asn Gly Leu Val
        195                 200                 205

Asp Gly Ile Ser Gly Asn Trp Tyr Cys Lys Phe Asp Thr Phe Thr Pro
    210                 215                 220

Ala Val Glu Arg Gly Leu Pro Val Thr Arg Val Ile Ser Arg Met Thr
225                 230                 235                 240

Leu Gln Gln Ile Leu Ala Arg Ala Val Gly Glu Asp Val Ile Met Asn
                245                 250                 255

Glu Ser Asn Val Val Asn Phe Glu Asp Asp Gly Glu Lys Val Thr Val
            260                 265                 270

Val Leu Glu Asn Gly Gln Arg Phe Thr Gly Asp Leu Leu Val Gly Ala
        275                 280                 285

Asp Gly Ile Arg Ser Lys Val Arg Thr Asn Leu Phe Gly His Ser Glu
    290                 295                 300

Ala Thr Tyr Ser Gly Tyr Thr Cys Tyr Thr Gly Ile Ala Asp Phe Val
305                 310                 315                 320

Pro Ala Asp Ile Asp Thr Val Gly Tyr Arg Val Phe Leu Gly His Lys
                325                 330                 335

Gln Tyr Phe Val Ser Ser Asp Val Gly Gly Gly Lys Met Gln Trp Tyr
            340                 345                 350

Ala Phe His Asn Glu Pro Ala Gly Gly Val Asp Ala Pro Asn Gly Lys
        355                 360                 365

Lys Glu Arg Leu Leu Lys Ile Phe Gly Gly Trp Cys Asp Asn Val Ile
    370                 375                 380

Asp Leu Leu Val Ala Thr Asp Glu Asp Ala Ile Leu Arg Arg Asp Ile
385                 390                 395                 400

Tyr Asp Arg Pro Pro Thr Phe Asn Trp Gly Arg Gly Arg Val Thr Leu
                405                 410                 415

Leu Gly Asp Ser Val His Ala Met Gln Pro Asn Leu Gly Gln Gly Gly
            420                 425                 430

Cys Met Ala Ile Glu Asp Ser Tyr Gln Leu Ala Leu Glu Leu Glu Lys
        435                 440                 445

Ala Trp Ser Arg Ser Ala Glu Ser Gly Ser Pro Met Asp Val Ile Ser
    450                 455                 460

Ser Leu Arg Ser Tyr Glu Ser Ala Arg Lys Leu Arg Val Gly Val Ile
465                 470                 475                 480

His Gly Leu Ala Arg Met Ala Ala Ile Met Ala Ser Thr Tyr Lys Ala
                485                 490                 495

Tyr Leu Gly Val Gly Leu Gly Pro Leu Ser Phe Leu Thr Lys Tyr Arg
            500                 505                 510
```

-continued

```
Ile Pro His Pro Gly Arg Val Gly Gly Arg Val Phe Val Asp Leu Gly
        515                 520                 525

Met Pro Leu Met Leu Ser Trp Val Leu Gly Gly Asn Gly Asp Lys Leu
    530                 535                 540

Glu Gly Arg Ile Gln His Cys Arg Leu Ser Glu Lys Ala Asn Asp Gln
545                 550                 555                 560

Leu Arg Arg Trp Phe Glu Asp Asp Asp Ala Leu Glu Arg Ala Thr Asp
                565                 570                 575

Ala Glu Trp Leu Leu Leu Pro Ala Ala Asn Gly Asn Ser Ala Leu Glu
            580                 585                 590

Thr Ile Val Leu Ser Arg Asp Glu Asp Val Pro Cys Thr Ile Gly Ser
        595                 600                 605

Val Ser His Thr Asn Ile Pro Gly Lys Ser Val Val Leu Pro Leu Pro
    610                 615                 620

Gln Val Ser Glu Met His Ala Gln Ile Ser Cys Lys Asn Asn Ala Phe
625                 630                 635                 640

Phe Val Thr Asp Phe Gln Ser Glu His Gly Thr Trp Val Ile Asp Asn
                645                 650                 655

Glu Gly Arg Arg Tyr Arg Val Ser Pro Asn Phe Pro Met Arg Phe His
            660                 665                 670

Ser Ser Asp Val Ile Val Phe Gly Ser Asp Lys Ala Ala Phe Arg Val
        675                 680                 685

Lys Thr Met Lys Phe Pro Ser Lys Thr Ala Glu Ala Lys Glu Glu Arg
    690                 695                 700

Lys Val Val Gly Thr Ala
705                 710
```

TRANSFORMANT AND METHOD FOR PRODUCING CAROTENOID COMPOSITION USING SAME

REFERENCE TO SEQUENCE LISTING

The present application is being filed along with a Sequence Listing in electronic format. The Sequence Listing is provided as a file entitled 57600693_1.TXT, created and last modified on May 11, 2023, which is 36.2 Kb in size. The information in the electronic format of the Sequence Listing is incorporated herein by reference in its entirety.

TECHNICAL FIELD

The present invention relates to a transformant and a method for producing a carotenoid composition using the same.

BACKGROUND ART

Carotenoids are natural pigments produced by plants, algae, bacteria, and the like, and are an important group of compounds that control various physiological functions in organisms. Many carotenoids have been isolated so far, and the health function of carotenoids, which are present only in trace amounts in nature, has begun to attract attention, however, since the carotenoids are in trace amounts, commercial production thereof is expensive and difficult.

For this reason, in recent years, biotechnology research for inexpensively producing carotenoids with microorganisms has been actively conducted. Carotenoid biosynthetic pathways and biosynthesis genes in plants have been largely revealed by 2000. Many attempts have been made to identify genes involved in biosynthesis of carotenoids from upstream, prepare transformants in which the identified genes are introduced into microorganisms, and produce carotenoids by the transformants.

The microorganism that has been most studied as a host for carotenoid production is *E. coli*. *E. coli* synthesizes isopentenyl diphosphate (IPP) and dimethylallyl diphosphate (DMAPP), which is an isomer thereof, through a non-mevalonate pathway (MEP pathway) as a basic metabolic pathway of isoprenoids including carotenoids (Non Patent Document 1). The synthesized IPP and DMAPP are metabolized to geranyl diphosphate (GPP) and farnesyl diphosphate (FPP) by a continuous condensation reaction via a prenyl group transferase.

*Escherichia coli* is a carotenoid non-producing bacterium, and does not possess an enzyme gene necessary for carotenoid synthesis after FPP, however, it becomes possible to synthesize various carotenoids by incorporating therein carotenoid biosynthesis genes such as a geranylgeranyl pyrophosphate (GGPP) synthase gene (crtE), a phytoene synthase gene (crtB), a phytoene desaturase gene (crtI) that synthesizes lycopene, a lycopene cyclase gene (crtY) that synthesizes β-carotene, and a β-carotene hydroxylase gene (crtZ) that synthesizes β-cryptoxanthin and zeaxanthin from the upstream depending on the carotenoid intended to be produced.

On the other hand, even if the carotenoid is found to be producible in this way, the actual production amount is often far from the practical production level simply by introducing a biosynthesis gene group of the carotenoid. This is attributed to the fact that *E. coli* can produce only a small amount of FPP as a precursor of carotenoid synthesis. For this reason, for mass production of carotenoids, pathway engineering for the purpose of increasing FPP production has been studied.

The approach of the pathway engineering is roughly divided into a method of modifying an endogenous metabolic pathway including the MEP pathway and a method of introducing a mevalonate (MVA) pathway gene group derived from a heterologous organism.

As a representative example of the former approach, there is a method of remarkably increasing the carotenoid production amount with *E. coli* in which a type 1 IPP isomerase gene (idi) derived from *S. cerevisiae* or *Haematococcus pluvialis* is highly expressed (Non-Patent Document 2), and for example, it has been reported that *E. coli* in which idi and, crtE, crtB, crtI, crtY, and crtZ derived from *Pantoea ananatis* are introduced can predominantly produce zeaxanthin (Non-Patent Document 3).

As a representative example of the latter approach, it has been found that deuterated zeaxanthin is synthesized using deuterated D-MVA lactone as a substrate by utilizing *E. coli* in which an MVA pathway gene group (including a type 2 IPP isomerase gene) derived from an actinomycete *Streptomyces* sp. CL190 strain is functionally expressed (Non-Patent Document 4). This approach is believed to be a powerful and effective means in pathway engineering studies for *E. coli*-hosted carotenoid production (Non-Patent Document 5).

On the other hand, it has been found that a zeaxanthin epoxidase (ZEP) gene synthesizes antheraxanthin from zeaxanthin, and a capsanthin-capsorubin synthase (CCS) gene synthesizes capsanthin from antheraxanthin, respectively, (Non Patent Document 6). However, there is no report that capsanthin was synthesized by introducing these genes into a host together with other carotenoid biosynthesis genes although it has been a long time since these genes were found.

PRIOR ART DOCUMENTS

Non-Patent Documents

Non-Patent Document 1: Rohmer, M. et al.: Biochem. J., 295, 517 (1993)

Non-Patent Document 2: Kajiwara, S. et al.: Biochem. J., 324, 421 (1997)

Non-Patent Document 3: Takemura, M. et al.: Tetrahedron Letters 56, 6063 (2015).

Non-Patent Document 4: Kakinuma, K. et al.: J. Am. Chem. Soc., 123, 1238 (2001).

Non-Patent Document 5: Journal of the Society for Biotechnology, Japan, Vol. 93, No. 7, 397 (2015).

Non-Patent Document 6: Bouvier, F. et al. The Plant Journal, 6 (1), 45 (1994)

SUMMARY OF THE INVENTION

Problems to be Solved by the Invention

Unlike lycopene, carotene, cryptoxanthin, and zeaxanthin, capsanthin cannot be synthesized by a method using a known recombinant microorganism. In fact, when the present inventors introduced CrtE gene, CrtB gene, CrtI gene, CrtY gene, CrtZ gene, ZEP gene, and CCS gene together with IDI gene into *E. coli*, capsanthin was not produced at all.

An object of the present invention is to provide a technique for producing a composition containing a carotenoid that has not been able to be synthesized so far, such as capsanthin, by a genetic recombination technique.

Means for Solving the Problem

The present inventor has conceived a novel idea of controlling the expression levels of only some genes in the biosynthesis gene group of capsanthin to be relatively high. Therefore, in order to obtain a relatively large amount of capsanthin substrate, a recombinant vector was constructed so that the expression level of the upstream gene in the biosynthesis gene group of capsanthin was relatively large, and this was transformed to try to synthesize capsanthin. However, in this method, incorporation of idi did not produce capsanthin at all.

Therefore, when the idea was changed so as to construct a recombinant vector so that the expression level of a downstream gene in the biosynthesis gene group of capsanthin becomes relatively high, it was unexpectedly found that the transformant can produce capsanthin. Furthermore, it was also unexpectedly found that when the ZEP gene and the CCS gene are incorporated into a recombinant vector such that the ZEP and the CCS are expressed so as to be indirectly bound via a multimer of a predetermined affinity protein, other various carotenoids such as capsorubin, cucurbitaxanthin A, and the like can also be produced. The present invention has been completed by further conducting studies based on this finding.

That is, the present invention provides inventions of the following aspects.

Item 1. A transformant in which a first promoter, and an upstream gene of a carotenoid biosynthesis gene including crtY and crtZ operably linked to the first promoter, and a second promoter having a higher promoter intensity than that the first promoter, and a ZEP gene and a CCS gene operably linked to the second promoter have been introduced into a host cell.

Item 2. The transformant according to item 1, wherein a difference in promoter intensity between the first promoter and the second promoter is equal to or greater than a difference in promoter intensity between a promoter unique to a carotenoid biosynthesis gene and PBAD.

Item 3. The transformant according to item 1 or 2, wherein the upstream gene further contains crtI; crtI and crtB; or crtI, crtB and crtE.

Item 4. The transformant according to any one of items 1 to 3, wherein the first promoter is Plac or a promoter unique to a carotenoid biosynthesis gene.

Item 5. The transformant according to any one of items 1 to 4, wherein the second promoter is PBAD or Ptac.

Item 6. The transformant according to any one of items 1 to 5, wherein additionally, an S protein gene, an S tag gene, and a linker gene have been introduced into the host cell, the S-tag gene is linked to each of the ZEP gene and the CCS gene, and the linker gene is interposed and linked between the ZEP gene and the S-tag gene and/or between the CCS gene and the S-tag gene.

Item 7. The transformant according to item 6, wherein the S-tag encoded by the S-tag gene is any one of the following polypeptides (1) and (2): (1) a polypeptide containing a base sequence encoding the amino acid sequence set forth in SEQ ID NO: 4; (2) a polypeptide that has a sequence identity of 90% or more other than the 12th sequence with respect to the amino acid sequence set forth in SEQ ID NO: 4 and specifically binds to S protein.

Item 8. The transformant according to any one of items 1 to 7, wherein the linker gene is interposed and linked at least between the ZEP gene and the S-tag gene.

Item 9. The transformant according to any one of items 1 to 8, wherein the linker gene is interposed and linked between the ZEP gene and the S-tag gene, and is not interposed between the CCS gene and the S-tag gene.

Item 10. A method for producing a carotenoid composition, including a step of culturing the transformant according to any one of items 1 to 9.

Item 11. The production method according to item 10, wherein the carotenoid composition contains capsanthin.

Item 12. The production method according to item 10 or 11, wherein the carotenoid composition contains capsorubin, capsanthin 3'-acetate, capsorubin 3-acetate, cucurbitaxanthin A, capsorubin diacetate, capsanthin 3,6-epoxide, and/or capsanthin 3,6-epoxide 3'-acetate.

Advantages of the Invention

According to the present invention, it is possible to produce a composition containing a carotenoid that has not been able to be synthesized so far, such as capsanthin, by a genetic recombination technique. The mechanism by which such an effect is obtained is not clear, but is considered as follows. For CCS, not only the activity of synthesizing capsanthin from antheraxanthin, but also the side activity of synthesizing β carotene from lycopene upstream of the carotenoid biosynthetic pathway was found. For this reason, it is considered that when the amount of the upstream substrate was increased, most of the functions of CCS were utilized as a catalyst for a reaction for synthesizing β carotene from lycopene, and the CCS did not function to exhibit the activity of synthesizing capsanthin. It is considered that the expression levels of zeaxanthin and the gene upstream thereof are relatively lowered, and the expression levels of the ZEP gene and the CCS gene downstream of the gene related to the synthesis of zeaxanthin are increased, so that excessive accumulation of zeaxanthin and the intermediate upstream thereof is suppressed, and CCS that has not been able to function to exhibit the activity of synthesizing capsanthin can be caused to function for the first time.

EMBODIMENTS OF THE INVENTION

1. Transformant

The transformant of the present invention is a transformant in which a first promoter, an upstream gene of a carotenoid biosynthesis gene including crtY and crtZ operably linked to the first promoter, a second promoter having a higher promoter intensity than the first promoter, and a ZEP gene and a CCS gene operably linked to the second promoter have been introduced into a host cell. This allows for the expression of a carotenoid biosynthesis enzyme in a host cell and the production of a carotenoid composition.

1-1. Carotenoid Biosynthesis Enzyme and Gene Encoding the Same (Carotenoid Biosynthesis Gene)

Figure 1:
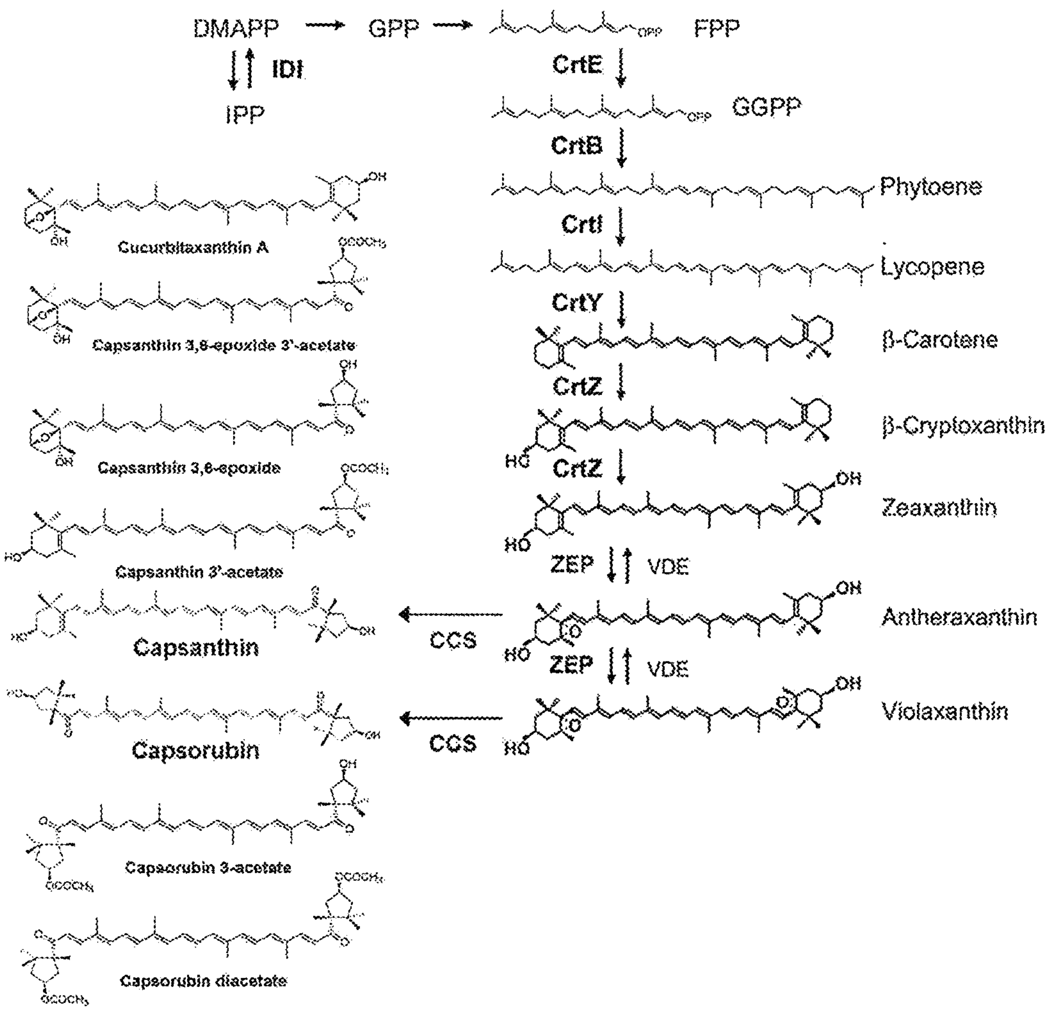
FIG. 1 shows a carotenoid biosynthetic pathway and a group of enzymes mediating the pathway.

FIG. 1 shows a carotenoid biosynthetic pathway and a group of enzymes mediating the pathway. FIG. 1 shows an example in which a carotenoid is biosynthesized using recombinant *E. coli.*

CrtE is a GGPP synthase that synthesizes geranylgeranyl pyrophosphate (GGPP) from farnesyl diphosphate (FPP), and hereinafter, the gene encoding CrtE is referred to as "crtE".

CrtB is a phytoene synthase that synthesizes phytoene from GGPP, and hereinafter, the gene encoding CrtB is described as "crtB".

CrtI is a phytoene desaturase that synthesizes lycopene from phytoene, and hereinafter, the gene encoding CrtI is referred to as "crtI".

CrtY is a lycopene cyclase that synthesizes β carotene from lycopene, and hereinafter, the gene encoding CrtY is described as "crtY".

CrtZ is a β-carotene hydroxylase that synthesizes β-cryptoxanthin and zeaxanthin from β-carotene, and hereinafter, the gene encoding CrtZ is referred to as "crtZ".

ZEP is a zeaxanthin epoxidase that synthesizes antheraxanthin and violaxanthin from zeaxanthin.

CCS is a capsanthin/capsorubin synthase known to synthesize capsanthin and capsorubin from antheraxanthin and violaxanthin, respectively. Furthermore, according to findings found by the present inventors, CCS is also a synthase that synthesizes capsanthin 3'-acetate and cucurbitaxanthin A from antheraxanthin, and synthesizes capsorubin 3-acetate, capsorubin diacetate, capsanthin 3,6-epoxide, and capsanthin 3,6-epoxide 3'-acetate from violaxanthin.

The gene encoding the carotenoid biosynthesis enzyme is a known gene, and its specific sequence can be appropriately obtained from the official database and the like.

The organism from which these carotenoid biosynthesis genes are derived is not particularly limited, and is selected without particular limitation from organisms that produce carotenoids corresponding to these genes. Specific origin organisms may be any plant or microorganism, and specifically include *Capsicum* (e.g., *Capsicum annuum*), *Lilium* (e.g., *Lilium lancifolium*), *Arabidopsis* (e.g., *Arabidopsis thaliana*), *Zea* (e.g., *Zea Mays*), *Prunus* (e.g., *Prunus armeniaca*), *Ipomoea* (e.g., *Ipomoea nil*), *Gentiana* (e.g., *Gentiana lutea*), *Marchantia* (e.g., *Marchantia polymorpha*), *Pantoea* (e.g., *Pantoea ananas*), *Agrobacterium* (e.g., *Agrobacterium aurantiacum*), *Heamatococcus, Monoraphidium, Phaffia* (*Xanthophyllomyces*), *Paracoccus, Brevundimonas, Gordonia* (*Rhodococcus*), *Nostoc, Brevundimonas*, Gloeobacter, and the like, and preferably include *Capsicum, Lilium*, and *Pantoea*. In addition, the difference of the organism from which each gene is derived is not limited, but the same organism is preferable.

The carotenoid biosynthesis gene that can be used in the present invention includes not only those consisting of a base sequence that can be obtained from the official database and a codon optimized sequence thereof, but also those consisting of a base sequence similar to (specifically, similar to the degree of similarity of the base sequences of (I-2), (II-2), (III-2), and (I-3), (II-3), and (III-3) to the base sequences of (I-1), (II-1), and (III-1) below) the sequence as long as they encode an enzyme having carotenoid biosynthesis enzyme activity.

Preferable examples of the base sequence of the carotenoid biosynthesis gene include the following.

(I-1) Base sequences of the crtE, crtY, crtI, crtB, and crtZ genes represented by DDBJ Accession No. D90087, (II-1) A base sequence of the ZEP gene represented by DDBJ accession number XM_016705616, (III-1) A base sequence of the CCS gene represented by DDBJ Accession No. X76165, (I-2) A base sequence of a nucleic acid that is a gene encoding each of an enzyme having GGPP synthase activity that synthesizes geranylgeranyl pyrophosphate (GGPP) from farnesyl diphosphate (FPP), an enzyme having phytoene synthase activity that synthesizes phytoene from GGPP, an enzyme having phytoene desaturase activity that synthesizes lycopene from phytoene, an enzyme having lycopene cyclase activity that synthesizes β carotene from lycopene, and an enzyme having β carotene hydroxylase activity that synthesizes β cryptoxanthin and zeaxanthin from β carotene, and being a base sequence of a nucleic acid hybridizing under stringent conditions with a nucleic acid containing base sequences complementary to the base sequences shown in the above (I-1), respectively, (II-2) A base sequence of a nucleic acid that is a gene encoding an enzyme having zeaxanthin epoxidase activity that synthesizes antheraxanthin and violaxanthin from zeaxanthin, and being a base sequence of a nucleic acid hybridizing under stringent conditions with a nucleic acid containing base sequences complementary to the base sequences shown in the above (II-1), (III-2) A base sequence of a nucleic acid that is a gene encoding enzymatic activity that synthesizes capsanthin and capsorubin from antheraxanthin and violaxanthin, respectively, and synthesizes, additionally, capsorubin, capsanthin 3'-acetate, capsorubin 3-acetate, cucurbitaxanthin A, capsorubin diacetate, capsanthin 3,6-epoxide, and capsanthin 3,6-epoxide 3'-acetate, and being a base sequence of a nucleic acid hybridizing under stringent conditions with a nucleic acid containing base sequences complementary to the base sequences shown in the above (III-1), (I-3) A base sequence that is a gene encoding each of an enzyme having GGPP synthase activity that synthesizes geranylgeranyl pyrophosphate (GGPP) from farnesyl diphosphate (FPP), an enzyme having phytoene synthase activity that synthesizes phytoene from GGPP, an enzyme having phytoene desaturase activity that synthesizes lycopene from phytoene, an enzyme having lycopene cyclase activity that synthesizes R carotene from lycopene, and an enzyme having β carotene hydroxylase activity that synthesizes β cryptoxanthin and zeaxanthin from β carotene, and having 90% or more homology with each of base sequences complementary to the base sequences shown in the above (I-1), (II-3) A base sequence that is a gene encoding an enzyme having zeaxanthin epoxidase activity that synthesizes antheraxanthin and violaxanthin from zeaxanthin, and having 90% or more homology with the base sequences shown in the above (II-1), (III-3) A base sequence that is a gene encoding enzymatic activity that synthesizes capsanthin and capsorubin from antheraxanthin and violaxanthin, respectively, and synthesizes, additionally, capsorubin, capsanthin 3'-acetate, capsorubin 3-acetate, cucurbitaxanthin A, capsorubin diacetate, capsanthin 3,6-epoxide, and capsanthin 3,6-epoxide 3'-acetate, and having 90% or more homology with the base sequences shown in the above (III-1).

In the above (I-2), (II-2), and (III-2), the phrase "under stringent conditions" refers to conditions for incubating for 4 hours to overnight at 50° C. to 65° C. in 6×SSC (1×SSC denotes 0.15 M NaCl, 0.015 M sodium citrate, pH 7.0) containing 0.5% SDS, 5×Denhartz's [Denhartz's, 0.1% Bovine Serum Albumin (BSA), 0.1% Polyvinylpyrrolidone, 0.1% Ficoll 400], and 100 μg/ml salmon sperm DNA. Hybridization under stringent conditions is specifically performed by the following method. That is, a nylon membrane on which a DNA library or a cDNA library is immobilized is prepared, and the nylon membrane is blocked at 65° C. in a prehybridization solution containing 6×SSC, 0.5% SDS, 5×Denhartz's, and 100 μg/ml salmon sperm DNA. Each probe labeled with $^{32}P$ is then added and incubated overnight at 65° C. This nylon membrane is washed in 6×SSC for 10 minutes at room temperature, in 2×SSC containing 0.1% SDS for 10 minutes at room temperature, in 0.2×SSC containing 0.1% SDS at 45° C. for 30 minutes, and then autoradiography is performed, and a nucleic acid specifically hybridized with the probe can be detected.

In the above (I-3), (II-3), and (III-3), the homology may be 90% or higher, preferably 95% or higher, more preferably 98% or higher, and still more preferably 98.5% or more, more preferably 99% or more, even more preferably 99.5% or more, and particularly preferably 99.9% or more. "Homology" is calculated using publicly available or commercially available software with algorithms that compare a reference sequence as a query sequence. Specifically, BLAST, FASTA, GENETYX (manufactured by GENETYX CORPORATION), and the like can be used, and these may be used by being set as default parameters.

Furthermore, in the carotenoid biosynthesis gene described above, the full-length sequence may be incorporated into a recombinant vector, or may be incorporated into a recombinant vector in a state in which an unnecessary sequence in expression of a target enzyme in a host is removed. For example, when the organism from which the carotenoid biosynthesis gene is derived is a plant and the host is a non-plant cell, it is preferable to incorporate the carotenoid biosynthesis gene into the recombinant vector in a state where the signal sequence is removed from the viewpoint of further improving the production amount of capsanthin. The signal sequence of each plant-derived gene can also be easily acquired by using the official database or various gene analysis tools.

In the carotenoid biosynthesis gene group, crtE, crtB, crtI, crtY, and crtZ are classified into "upstream genes", and the ZEP gene and the CCS gene are classified into "downstream genes", in the following.

The upstream gene of the carotenoid biosynthesis gene is operably linked to a first promoter and the downstream gene of the carotenoid biosynthesis gene is operably linked to a second promoter. That is, the first promoter is a region that performs transcription control of an upstream gene, and the second promoter is a region that performs transcription control of a downstream gene. Operably linked means that the control factor and the above gene are linked in a state where they can operate in the host cell.

1-2. Promoter

Regarding the relationship between the first promoter and the second promoter, the second promoter is designed to have a higher promoter intensity than the first promoter. For example, the promoter intensity of the second promoter is preferably three times or more the promoter intensity of the first promoter. Promoter intensity refers to the frequency of transfer initiation, and is measured, for example, in Pbla unit (Pbla unit; Deuschle et al., EMBO J., 5: 2987-2994 (1986)), in miller unit (Miller units; also referred to as β-galactosidase unit; 5000 times the Pbla unit (Lanzer et al., PNAS USA, 85, 8973-8977 (1988)), RPU (Relative promoter units; Meyer et al., Nature Chemical Biology 15, 196-204 (2019)), or the like.

In the present invention, the first promoter and the second promoter control the expression level of the upstream gene of the carotenoid biosynthesis gene so as to be relatively low and the expression level of the downstream gene so as to be relatively high, thereby allowing the synthesis of the carotenoid.

From the viewpoint of further improving the synthesis amount of the carotenoid, the difference in promoter intensity between the first promoter and the second promoter is preferably greater than or equal to the difference in promoter intensity between the promoter unique to the carotenoid biosynthesis gene (preferably a promoter which is naturally present in *Pantoea ananatis*, more preferably a promoter which is included in DDBJ accession number D90087) and the PBAD promoter, and more preferably greater than or equal to the difference in promoter intensity between the promoter unique to the carotenoid biosynthesis gene (preferably a promoter which is naturally present in *Pantoea ananatis*, more preferably a promoter which is included in DDBJ accession number D90087) and the tac promoter.

The first promoter and the second promoter are not particularly limited as long as they are designed so that the second promoter has a relatively higher promoter intensity, and are appropriately selected according to the type of the host into which the recombinant vector incorporating these promoters is introduced. The first promoter and the second promoter may be natural promoters or artificial promoters.

Specific examples of the promoter used as the first promoter and the second promoter include a lac promoter (Plac), a promoter unique to the carotenoid biosynthesis gene, a BAD promoter (PBAD), a tac promoter (Ptac), a trc promoter, a T7 promoter, a T71ac promoter, a T5 promoter, a UV51ac promoter, a L8-UV51ac promoter, a cspA promoter, a CAG promoter, a CMV promoter, an RSV promoter, and the like, in prokaryotes such as *E. coli* and the like, and include a GAL1 promoter, an NMT1 promoter, a TEF1 promoter, an ADH1 promoter, a TPI1 promoter, an HXT7 promoter, a TDH3 promoter, a PGK1 promoter, a PYK1 promoter, a CAG promoter, a CMV promoter, an RSV promoter, and the like, in yeasts.

The promoter unique to the carotenoid biosynthesis gene is a promoter that is naturally provided in the biosynthesis of carotenoid. The promoter unique to the carotenoid biosynthesis gene can be used without particular limitation, and in the organism from which the carotenoid biosynthesis gene is derived, a promoter that is naturally provided as a promoter of the carotenoid biosynthesis gene can be used. As an example, in a case where the gene placed under the control of the promoter unique to the carotenoid biosynthesis gene is derived from *Pantoea ananatis*, preferably a promoter naturally provided in *Pantoea ananatis*, more preferably a promoter included in DDBJ accession number D90087 can be used as the promoter unique to the carotenoid biosynthesis gene.

Among various promoters including these examples, two types having different promoter intensities can be selected, and the one having a higher promoter intensity can be selected as the first promoter and the one having a lower promoter intensity can be selected as the second promoter. Furthermore, in order to further improve the synthesis amount of the carotenoid, a combination of two promoters can be selected from among various promoters including the above examples so that the promoter intensities show the difference in promoter intensity described above, and the one with the lower promoter intensity can be selected as the first promoter and the one with the higher promoter intensity can be selected as the second promoter.

More preferably, examples of the first promoter include Plac and promoters unique to carotenoid biosynthesis genes, and examples of the second promoter include PBAD and Ptac, and even more preferably Ptac.

In addition, the control of the expression level by using the first promoter and the second promoter having different promoter intensities as described above is performed so as to suppress the reaction of synthesizing β carotene from lycopene by CCS. Therefore, the upstream gene expressed by the first promoter should include at least crtY and crtZ.

Other upstream genes may be placed under the control of the first promoter as with crtY and crtZ, or may be placed under the control of other promoters. Preferably, the other upstream gene is preferably placed under the control of the first promoter. A specific example of a case where another upstream gene is placed under the control of the first promoter is a case where (i) crtI is further contained; a case where (ii) crtI and crtB are contained; and a case where (iii) crtI, crtB, and crtE are contained, as the upstream gene. In addition, IPP isomerase gene (idi) may be contained together with other upstream genes, that is, (iv) crtI, crtB, crtE, and idi may be further placed under the control of the first promoter.

Both the first promoter and the gene placed under the control thereof and the second promoter and the gene placed under the control thereof may be incorporated into one expression vector to constitute one recombinant vector, or may be incorporated into separate expression vectors to constitute the first recombinant vector and the second recombinant vector, respectively.

1-3. Gene for Expression of Cooperative System of CCS and ZEP Via S Protein

Figure 12:
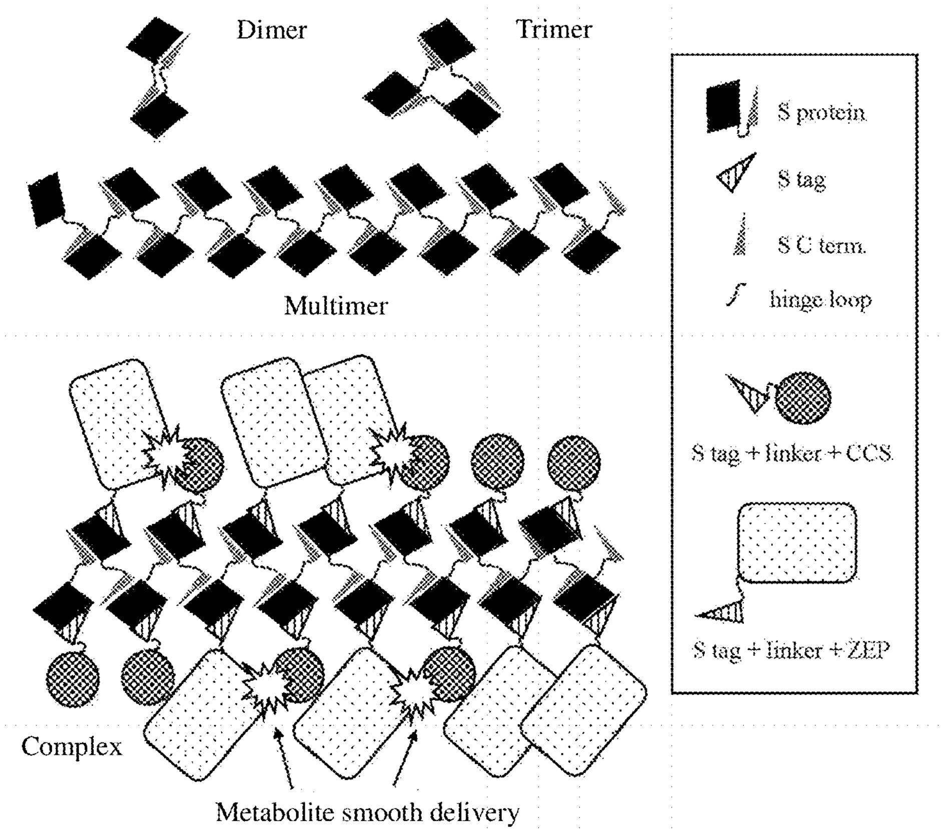
FIG. 12 schematically shows a cooperative system of CCS and ZEP using S protein constructed in an expression system according to Example 3 (Example 3-1 to Example 3-3).

CCS also has lycopene β-cyclase activity possessed by CrtY in addition to capsanthin/capsorubin synthesis activity. Due to such dual activity of CCS, even if the CCS gene is efficiently expressed in *E. coli*, a reaction of receiving lycopene as a substrate from CrtI and synthesizing β-carotene by acting in cooperation with phytoene desaturase CrtI rather than ZEP may be prioritized. Therefore, in order to further increase the production amount of a reaction product by CCS by selectively reacting CCS with ZEP in a cooperative manner, it is preferable that the CCS gene and the ZEP gene are introduced into the host cell in a mode in which a cooperative system of CCS and ZEP via S protein is expressed, as follows. FIG. 12 is a diagram schematically illustrating the cooperation system.

In an embodiment of the present invention in which a cooperative system of CCS and ZEP via S protein is expressed, further, an S protein gene, an S tag gene, and a linker gene are introduced into a host cell, the S tag gene is linked to each of the ZEP gene and the CCS gene, and the linker gene is interposed and linked between the ZEP gene and the S tag gene and/or between the CCS gene and the S tag gene.

The S-tag and the S-protein are in a mutually specific relationship of affinity tag and affinity protein, and are polypeptides constituting one RNase A molecule. An N-terminal 20 amino acid fragment obtained by cleaving RNase A with subtilisin is an S tag, and a remaining fragment composed of about 100 amino acids is an S protein. The S-tag and S-protein can be non-covalently bound to reproduce the original conformation, resulting in RNase activity (Lopez-Alonso, J. P., Bruix, M., Font, J., Ribo, M., Vilanova, M., Rico, M., Gotte, G., Libonati, M., Gonzalez, C. and Laurents, D. V. (2006) J. Biol. Chem. 281, 9400-9406).

S protein and RNase A have a property that a part of these molecules swaps a C-terminal β-strand between molecules to form a multimer, such as a homo "dimer", a homo "trimer", or a trimer or more homo "multimer" as shown in FIG. 12.

On the other hand, the ZEP gene and the CCS gene to which the S-tag gene is linked are expressed as S-tag-fused ZEP and S-tag-fused CCS, respectively, in the host cell. Furthermore, since the linker gene is interposed and linked between the ZEP gene and the S-tag gene and/or between the CCS gene and the S-tag gene, either or both of the S-tag-fused ZEP and S-tag-fused CCS expressed in the host cell take the form of a fusion protein via a linker between the S-tag and the enzyme. In the schematic diagram of FIG. 1, an example is shown in which both the S-tag-fused ZEP and the S-tag-fused CCS are expressed in the form of a fusion protein via a linker between the S-tag and the enzyme (In the figure, "S tag+linker+CCS" and "S tag+linker+ZEP" are illustrated).

Since such an S-tag-fused ZEP and S-tag-fused CCS are co-expressed with S protein, a complex in which the fused ZEP and the fused CCS are indirectly bound to the S protein multimer via the S tag is formed as shown in FIG. 12. By forming such a complex, the ZEP and the CCS physically approach each other in the host cell, so that the CCS can selectively cooperatively react with the ZEP. That is, the CCS can smoothly receive metabolites by the ZEP. This makes it possible to obtain more carotenoids produced by CCS metabolism. More specifically, it is possible to increase the amount of capsanthin produced and/or to increase the amount of capsorubin, capsanthin 3'-acetate, capsorubin 3-acetate, cucurbitaxanthin A, capsorubin diacetate, capsanthin 3,6-epoxide, and/or capsanthin 3,6-epoxide 3'-acetate produced.

As described above, S protein is known as a cleavage product of about 100 amino acids by subtilisin of RNase A, and thus its amino acid sequence is known (specific examples thereof include SEQ ID NO: 2), and the base sequence of S protein gene is also known (specific examples thereof include SEQ ID NO: 1). Examples of the base sequence of the S protein gene that can be used in the present invention include the following.

(IV-1) A base sequence represented by SEQ ID NO: 1, (IV-2) A base sequence of a nucleic acid that is a gene encoding a protein that forms a multimer and specifically binds to an S tag, and being a base sequence of a nucleic acid hybridizing under stringent conditions with a nucleic acid containing base sequences complementary to the base sequences shown in the above (IV-1), and (IV-3) A base sequence that is a gene encoding a protein that forms a multimer and specifically binds to an S tag, and having 90% or more homology with the base sequences shown in the above (IV-1).

The phrase "under stringent conditions" in the above (IV-2) is the same as those described for the above (I-2), (II-2), and (III-2). The "homology" in the above (IV-3) and preferred examples thereof are the same as those described in the above (I-3), (II-3), and (III-3).

As described above, the S-tag is known as a product of cleavage of 20 amino acids at the N-terminus of RNase A by subtilisin, and thus the amino acid sequence thereof is known (specific examples of the amino acid sequence include an amino acid sequence in which the 12th position of SEQ ID NO: 4 is histidine instead of phenylalanine), and the base sequence of the S protein gene is also known (specific examples thereof include a base sequence in which positions 34 to 36 of SEQ ID NO: 3 are sequences encoding histidine instead of the sequence encoding phenylalanine).

Examples of the S tag that can be used in the present invention include any of the following.

(1) A polypeptide containing a base sequence encoding the amino acid sequence set forth in SEQ ID NO: 4.

(2) A polypeptide that has a sequence identity other than the 12th sequence with respect to the amino acid sequence set forth in SEQ ID NO: 4 of 90% or more, preferably 95% or more, and specifically binds to S protein.

In the amino acid sequence set forth in SEQ ID NO: 4, the 12th amino acid sequence is substituted from histidine in the wild-type S-tag to phenylalanine for the purpose of suppressing the influence on RNase activity caused by binding of the S-tag to S protein in the host cell.

In the polypeptide of the above (2), the sequence identity to the amino acid sequence set forth in SEQ ID NO: 4 is a sequence identity calculated as compared with the amino acid sequence set forth in SEQ ID NO: 4. In addition, the "sequence identity" indicates a value of identity of an amino acid sequence obtained by bl2seq program (Tatiana A. Tatsusova, Thomas L. Madden, FEMS Microbiol. Lett., Vol. 174, p 247-250, 1999) of BLASTPACKAGE [sgi 32 bit edition, Version 2.0.12; available from National Center for Biotechnology Information (NCBI)]. The parameter may be set to Gap insertion Cost value: 11 and Gap extension Cost value: 1.

The base sequence of the S-tag gene that can be used in the present invention is not particularly limited as long as it is a base sequence encoding the S-tag, and preferred examples thereof include the following.

(V-1) A base sequence represented by SEQ ID NO: 3 (that is, a base sequence encoding the amino acid sequence represented by SEQ ID NO: 4), (V-2) A base sequence that is a gene encoding a peptide that specifically binds to S protein, and having 90% or more, preferably 95% or more homology with the base sequence shown in (V-1) above (with the proviso that the base sequence other than positions 34 to 36 of SEQ ID NO: 3).

The "homology" in the above (V-2) is the same as those described for the above (I-3), (II-3), and (III-3).

At positions 34 to 36 of SEQ ID NO: 3 in (V-1) to (V-2) of the S-tag gene, a sequence encoding histidine present in a wild-type S-tag is substituted with a sequence encoding phenylalanine for the purpose of suppressing an influence on RNase activity caused by binding of the expressed S-tag to S protein in a host cell.

In addition, the binding position of the S-tag gene is not particularly limited, but from the viewpoint of reducing the influence on the activity of the enzyme to be fused with the S-tag, the S-tag can be designed to bind to the N-terminal of the enzyme (ZEP and/or CCS).

The linker gene is not particularly limited as long as the linker (peptide) has an appropriate distance between the S-tag and the enzyme in the fusion protein, thereby ensuring the degree of freedom between CCS and ZEP in the complex. A preferred sequence of the linker (peptide) in the fusion protein is a sequence in which a nonpolar amino acid and a polar amino acid are alternately linked from the viewpoint of eliminating polarity bias of the linker (peptide) itself and suppressing undesired adsorption and the like, and a combination of the nonpolar amino acid and the polar amino acid is preferably a combination of glycine and serine. The length of the linker (peptide) is, for example, 15 to 25 amino acids, preferably 18 to 22 amino acids.

As described above, the interposing position of the linker gene may be at least one of between the ZEP gene and the S-tag gene and between the CCS gene and the S-tag gene, but is preferably at least between the ZEP gene and the S-tag gene, and particularly preferably only between the ZEP gene and the S-tag gene (not interposed between the CCS gene and the S-tag gene).

1-4. Other Genes

In addition to the sequences described above, the recombinant vector may contain regulatory sequences other than the first promoter and the second promoter. Such a regulatory sequence is positioned upstream (5' side), within, or downstream (3' side) of the sequence of the upstream gene of the carotenoid biosynthesis gene and/or the sequence of the downstream gene of the carotenoid biosynthesis gene, and affects transcription, RNA processing, stability, or the like. Examples of the regulatory sequence include a translation leader sequence, an intron, a polyadenylation recognition sequence, an RNA processing site, an effector binding site, a stem-loop structure, and the like.

1-5. Expression Vector

As the expression vector, a vector constructed for gene recombination from a plasmid, a virus, a phage, a transposon, an IS element, a phasmid, a cosmid, or the like capable of autonomously growing in a host can be used. Examples of such expression vectors include pET, pLG, pACYC, pBR, pUC, pKC, pRep, pHS, pKK, pDHE, pPLc, pMBL, pUR, pIN, λgt, pBdCI, pUB, pC, and pBD; pSA, pAJ, YEp, YRp, YIp, pYAC, pCDM, pMT2PC, an adenoviral vector, an adeno-associated viral vector, a retroviral vector, a herpesvirus vector, and the like. The underlying expression vectors may be the same or different between the first recombinant vector and the second recombinant vector. In addition, as the expression vector, an appropriate combination with a host cell may be selected and used, and for example, as a preferable example in the case of using *E. coli* as a host cell, a combination of a pACYC vector and a pUC vector with a JM101 (DE3) *E. coli* strain, and the like can be mentioned.

1-6. Host Cells

The host is not particularly limited as long as the recombinant vector is stable, can autonomously proliferate, and can express the trait of a foreign gene, and may be a carotenoid-producing cell or a carotenoid-non-producing cell. Preferred examples of the host include bacteria belonging to the genus *Escherichia* such as *Escherichia coli*, etc., the genus *Bacillus* such as *Bacillus subtilis*, etc., the genus *Pseudomonas* such as *Pseudomonas putida*, etc., and the like; yeasts (for example, budding yeast (*Saccharomyces cerevisiae*), fission yeast (*S. pombe*), torula yeast (*Candida utilis*), methanol-assimilating yeast (*Pichia pastoris*), red yeast (*Xanthophyllomyces dendrorhous*), etc.), and the like, but may also include animal cells, insect cells, plants, and the like. Among them, *E. coli* is a particularly preferred host.

1-7. Production of Transformant

The transformant of the present invention can be obtained by introducing a recombinant vector into a host, and conditions for introducing the recombinant vector into the host may be appropriately set according to the type of the host, and the like. When the host is a bacterium, examples thereof include a heat shock method, a method using a competent cell by calcium ion treatment, an electroporation method, and the like. When the host is a yeast, examples thereof include an electric boring method (electroporation method), a spheroplast method, a lithium acetate method, and the like. When the host is an animal cell, examples thereof include an electroporation method, a calcium phosphate method, a lipofection method, and the like. When the host is an insect cell, examples thereof include a calcium phosphate method, a lipofection method, an electroporation method, and the like. When the host is a plant cell, examples thereof include an electroporation method, an *Agrobacterium* method, a particle gun method, a PEG method, and the like.

Whether or not the recombinant vector has been incorporated into the host can be confirmed by a PCR method, a Southern hybridization method, a Northern hybridization method, or the like.

When it is confirmed whether or not the recombinant vector has been incorporated into the host by the PCR method, for example, the recombinant vector may be separated and purified from the transformant.

The separation and purification of the recombinant vector can be performed on the basis of a lysate obtained by lysing bacteria, for example, when the host is a bacterium. As a method of lysis, for example, treatment is performed with a lytic enzyme such as lysozyme or the like, and if necessary, a protease, other enzymes, and a surfactant such as sodium lauryl sulfate (SDS) or the like, are used in combination.

Furthermore, physical crushing methods such as freeze-thaw, ultrasonic irradiation and French press treatment may be combined. The separation and purification of DNA from the lysate can be performed, for example, by deproteinization by phenol treatment and protease treatment, ribonuclease treatment, alcohol precipitation treatment, and a commercially available kit being appropriately combined.

DNA cleavage can be performed according to a conventional method, for example, using restriction enzyme treatment. As the restriction enzyme, for example, a type II restriction enzyme that acts on a specific nucleotide sequence can be used. Binding between the DNA and the expression vector can be performed using, for example, a DNA ligase.

Thereafter, the separated and purified DNA is cut with a specific restriction enzyme, subjected to agarose gel electrophoresis, polyacrylamide gel electrophoresis, capillary electrophoresis, and the like, and stained with ethidium bromide, SYBR Green solution, and the like, and transformation can be confirmed from the detected band length pattern.

In addition, transformation can also be confirmed by designing primers and performing PCR using the isolated and purified DNA as a template. The amplification product obtained by PCR is subjected to agarose gel electrophoresis, polyacrylamide gel electrophoresis, capillary electrophoresis, or the like, stained with ethidium bromide, SYBR Green solution, or the like, and then the amplification product is detected as a band, whereby transformation can be confirmed.

In addition, PCR can be performed using a primer labeled with a fluorescent dye or the like in advance to detect an amplification product. Furthermore, a method of binding an amplification product to a solid phase such as a microplate or the like and confirming the amplification product by fluorescence, an enzymatic reaction, or the like may also be adopted.

2. Method for Producing Carotenoid Composition

The method for producing the carotenoid composition of the present invention can be obtained by a production method including a step of culturing the transformant of the present invention.

The culture conditions of the transformant may be appropriately set in consideration of the nutritional physiological properties of the host, and liquid culture is preferable. In the case of industrial production, aeration stirring culture is preferable.

As a nutrient source of the medium, those required for growth of transformants can be used. The carbon source may be any carbon compound that can be assimilated, and examples thereof include molasses, glucose, fructose, maltose, sucrose, lactose, sucrose, starch, lactose, glycerol, pyruvic acid, and the like.

The nitrogen source may be any assimilable nitrogen compound, and examples thereof include natural components such as corn steep liquor, peptones (meat peptone, casein peptone, soybean peptone, etc.), extracts (meat extract, yeast extract), and the like; ammonium salts such as ammonium acetate, ammonium chloride, ammonium sulfate, etc., amino acids such as glutamic acid, aspartic acid, glycine, etc.; and the like.

In addition to the carbon source and the nitrogen source, for example, phosphates, carbonates, sulfates, salts of magnesium, calcium, potassium, iron, manganese, zinc and the like, specific vitamins, and the like may be used as necessary.

The culture temperature can be appropriately set within a range in which the transformant of the present invention can grow and the transformant of the present invention produces the polypeptide of the present invention, but it is preferably about 20 to 40° C., preferably about 30 to 37° C. The culturing may be completed at an appropriate time with reference to the time when the polypeptide of the present invention reaches the highest yield, and examples of the culturing time include 24 to 200 hours, preferably about 60 to 90 hours.

Examples of the method for recovering the bacterial cells after completion of the culture include filtration, decantation, and centrifugation of the culture solution, and the like. The recovered bacterial cells can be treated with water, a sodium chloride solution, dimethylformamide, or the like as necessary.

The carotenoid composition obtained in the production method of the present invention typically contains capsanthin, preferably further contains capsorubin, capsanthin 3'-acetate, capsorubin 3-acetate, cucurbitaxanthin A, capsorubin diacetate, capsanthin 3,6-epoxide, and/or capsanthin 3,6-epoxide 3'-acetate.

For the extraction of the carotenoid composition from the bacterial cells, an appropriate organic solvent can be used. Examples of the organic solvent include methanol, ethanol, isopropyl alcohol, acetone, hexane, diethyl ether, tetrahydrofuran, methyl ethyl ketone, methyl isobutyl ketone, dichloromethane, chloroform, dimethylformamide, dimethyl sulfoxide, methyl acetate, ethyl acetate, and the like, and one or more of these solvents can be selected. Among these organic solvents, acetone, methanol, and diethyl ether are preferable.

The carotenoid composition fraction obtained as described above may be directly concentrated and dried as a composition, or each carotenoid can be purified, concentrated, and dried.

The purification method can be performed, for example, by appropriately combining methods such as gel filtration, adsorption chromatography, ion exchange chromatography, affinity chromatography, and the like. Examples of the drying method include freeze drying, vacuum drying, spray drying, and the like.

EXAMPLES

Hereinafter, the present invention will be described more specifically with reference to examples, but the present invention is not limited thereto. The promoter used in the following Examples and Comparative Examples includes Plac, promoters unique to the carotenoid biosynthesis gene (promoters naturally present in *Pantoea ananatis*, specifically promoters included in DDBJ accession number D90087), PBAD, or Ptac, and the relationship of promoter intensity is Plac<promoter unique to the carotenoid biosynthesis gene<PBAD<Ptac, and the promoter intensity of PBAD is three times or more the promoter intensity of the promoter unique to the carotenoid biosynthesis gene.

Comparative Example 1

Figure 2:
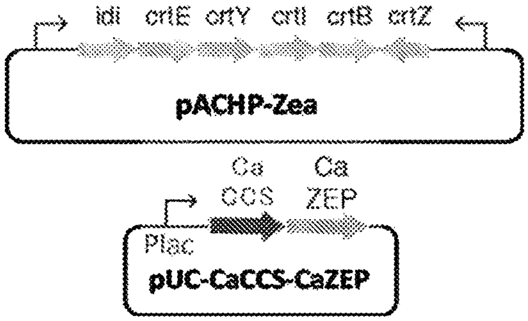
FIG. 2 is a schematic diagram of a recombinant vector produced in Comparative Example 1.

In this comparative example, pACHP-Zea shown in FIG. 2 was constructed as the first recombinant vector to be incorporated, and pUC-Plac-CaCCS-CaZEP shown in FIG. 2 was constructed as the second recombinant vector. These recombinant vectors were designed so that the expression level of upstream gene was relatively higher by the promoter unique to the carotenoid biosynthesis gene (derived from *Pantoea ananatis*), and the expression level of downstream gene was relatively lower by Plac. An outline of the first recombinant vector and the second recombinant vector of the present comparative example is shown in Table 1.

TABLE 1

| | Recombinant vector | Promoter | Promoter relative intensity | Vector constitution (abbreviation) |
|---|---|---|---|---|
| Comparative Example 1 | First | Derived from *pantoea ananatis* | High | pACHP-Zea |
| | Second | Plac | Low | pUC-Plac-CaCCS-CaZEP |

pACHP-Zea as the first recombinant vector is a vector for zeaxanthin synthesis used in the report of Non-Patent Document 3. pACHP-Zea is configured by inserting, into a pACYC vector, an idi gene derived from *Haematococcus pluvialis* (DDBJ Accession No. AB019034) and a gene group required for zeaxanthin biosynthesis (crtE, crtY, crtI, crtB, and crtZ genes derived from *Pantoea ananatis* (DDBJ accession number D90087)).

pUC-Plac-CaCCS-CaZEP as the second recombinant vector was produced by placing *Capsicum annuum*-derived ZEP gene (hereinafter, it is described as "CaZEP"; DDBJ accession number XM_016705616) and *Capsicum annuum*-derived CCS gene (hereinafter, referred to as "CaCCS"; DDBJ Accession No. X76165) downstream of the Plac-promoter of the pUC vector.

Both the first recombinant vector and the second recombinant vector were introduced into the *E. coli* JM109 strain by a heat shock method.

After introduction of the recombinant vector, single colonies on the LB medium were transplanted into 5 mL of LB liquid medium, and cultured with shaking at 200 rpm at 37° C. for 16 hours. A volume of 100 μL of the culture medium was transplanted into 10 mL of TB liquid medium, and after 24 hours of shaking culture at 200 rpm at 30° C., 10 μL of isopropyl-β-D-galactopyranoside (IPTG) was added to induce gene expression, and the culture was continued for 48 hours. Chloramphenicol (30 mg/L) and kanamycin (40 mg/L) as antibiotics were added to the medium.

A volume of 1 mL of the obtained culture solution was centrifuged at 8,000 g for 1 minute, and the supernatant was removed to collect a cell fraction. The cell fraction was suspended in 1% sodium chloride solution and centrifuged at 8,000 g for 1 minute, the supernatant was removed, and the cells were collected. To the collected cells was added 0.5 mL of acetone, 1 mL of diethyl ether/hexane (1:1 by volume) and vortexed vigorously. After 1 mL of water was added and stirred, the mixture was allowed to stand for 5 minutes, and the upper layer was collected in a 1.5 mL centrifugal tube and dried and solidified by a vacuum centrifugal concentrator.

The resulting dried solid was subjected to separation of carotenoids using Aquity H-class UPLC (Waters). Using Aquity UPLC BEH C18 column (2.1×100 mm, 1.7 μm, Waters) as a column, acetonitrile:ultrapure water (85:15 (volume basis)) as a mobile phase A, and acetonitrile: methanol (65:35 (volume basis)) as a mobile phase B, the mobile phase A and the mobile phase B were fed by gradient for 8 minutes such that the ratio of the mobile phase A:the mobile phase B was changed from 100:0 to 0:100. Thereafter, the carotenoid was separated by holding the ratio of 0:100 for 5 minutes.

As a result, a peak having the same elution time as that of the capsanthin sample could not be confirmed.

Comparative Example 2 (Comparative Example 2-1 and Comparative Example 2-2)

Figure 3:
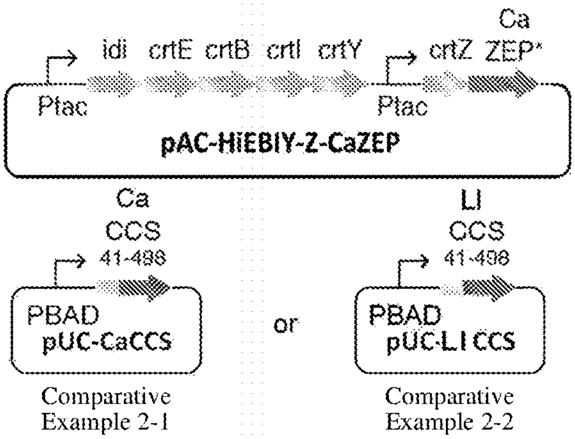
FIG. 3 is a schematic diagram of recombinant vectors produced in Comparative Example 2 (Comparative Example 2-1 and Comparative Example 2-2).

In this comparative example, pAC-HiEBIY-Z-CaZEP shown in FIG. 3 was constructed as the first recombinant vector to be incorporated, and pUC-CaCCS (The case of using this second recombinant vector is defined as Comparative Example 2-1) or pUC-LlCCS (The case of using this second recombinant vector is defined as Comparative Example 2-2) shown in FIG. 3 was constructed as the second recombinant vector. These recombinant vectors were designed so that the expression level of ZEP gene among upstream genes and downstream genes was relatively higher by Ptac, and the expression level of CCS gene among downstream genes was relatively lower by PBAD. An outline of the first recombinant vector and the second recombinant vector of the present comparative example is shown in Table 2.

TABLE 2

| | Recombinant vector | Promoter | Promoter relative intensity | Vector constitution (abbreviation) |
|---|---|---|---|---|
| Comparative Example 2-1 | First | Ptac | High | pAC-HiEBIY-Z-CaZEP(*1) (*1: $CaZEP_{64-668}$) |
| | Second | PBAD | Low | PUC-CaCCS(*2) (*2: $CaCCS_{41-498}$) |
| Comparative Example 2-2 | First | Ptac | High | pAC-HiEBIY-Z-CaZEP(*1) (*1: $CaZEP_{64-668}$) |
| | Second | PBAD | Low | pUC-LICCS(*2) (*2: $LICCS_{41-498}$) |

In Comparative Example 2-1 and Comparative Example 2-2, pAC-HiEBIY-Z-CaZEP in which the *Haematococcus pluvialis*-derived idi gene, and together, the respective genes crtE, crtB, crtI, crtY, and crtZ derived from *Pantoea ananatis* necessary for biolaxanthin biosynthesis, and the 64th to 668th amino acid residues (This is because a plant-derived gene often has a signal sequence unnecessary in *E. coli* at the N-terminal of a protein. It is abbreviated as $CaZEP_{64-668}$ and is denoted as ZEP* in FIG. 3) of CaZEP were placed downstream of the Ptac promoter, in a pACYC plasmid vector, was produced as a first recombinant vector on the basis of the report of Non-Patent Document 3.

The produced first recombinant vector pAC-HiEBIY-Z-CaZEP was introduced into *E. coli* JM101 (DE3) and cultured in the same manner as in Comparative Example 1 to obtain a supernatant.

The obtained supernatant was subjected to separation of carotenoids using HPLC Chromaster system manufactured by Hitachi, Ltd. Using Inertsil ODS-3 (4.6×150 mm, 5 μm, GL Sciences) as a column, acetonitrile as a mobile phase A, and isopropanol as a mobile phase B, the mobile phase A and the mobile phase B were fed at the ratio of 100:0 for 5 minutes, and then the mobile phase A and the mobile phase B were fed by gradient for 5 minutes such that the ratio of the mobile phaseA:the mobile phase B was changed from 100:0 to 50:50 (volume basis), and the ratio of 50:50 was further held for 5 minutes to separate carotenoids.

Figure 4:
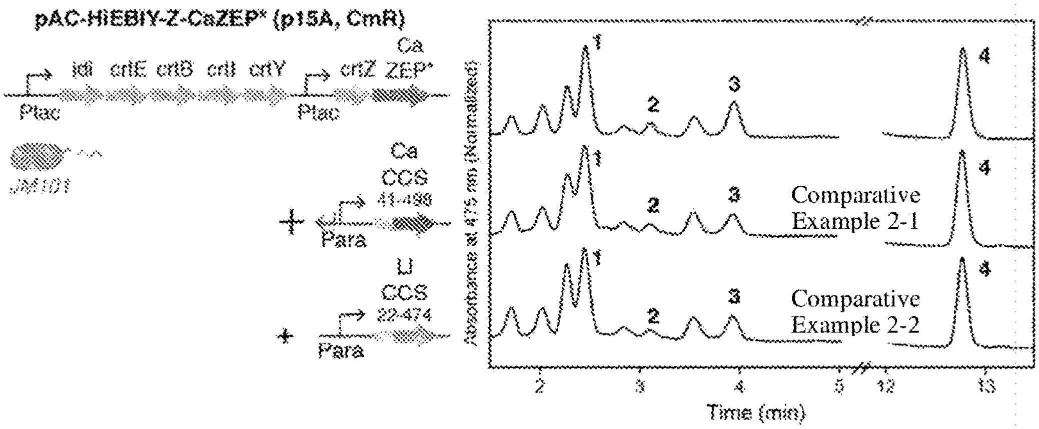
FIG. 4 shows an HPLC chromatogram of carotenoid compositions obtained in Comparative Example 2 (Comparative Example 2-1 and Comparative Example 2-2).
Figure 4:
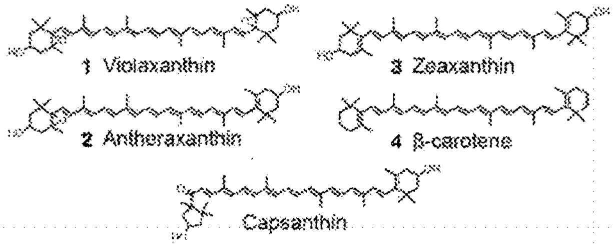

FIG. 4 shows the obtained HPLC chromatogram. As shown in FIG. 4, it was confirmed that zeaxanthin and O-carotene and many other carotenoid intermediates were produced in addition to violaxanthin and antheraxanthin.

Next, in Comparative Example 2-1 among Comparative Example 2-1 and Comparative Example 2-2, it was examined whether capsanthin and capsorubin could be produced by co-expressing CaCCS in this carotenoid producing *E. coli* strain. The N-terminal chloroplast signal sequence of CaCCS was predicted, and $CaCCS_{41-498}$ with the N-terminal amino acid deleted was designed. Plasmid pUC-CaCCS, in which $CaCCS_{41-498}$ was placed downstream of the PBAD promoter of the pUC vector, was prepared as a second recombinant vector and introduced into the carotenoid producing *E. coli* strain.

Further, in Comparative Example 2-2 among Comparative Example 2-1 and Comparative Example 2-2, pUC-LlCCS was produced as a second recombinant vector in the same manner as in Comparative Example 2-1, except that *Lilium lancifolium*-derived CCS (hereinafter referred to as "LlCCS"; DDBJ Accession No. GU443955) was introduced instead of CaCCS, and introduced into the above carotenoid-producing *E. coli* strain.

In Comparative Example 2-1 and Comparative Example 2-2, after introduction of the respective second recombinant vectors, the single colonies on the LB medium were transplanted into 3 mL of LB liquid medium, and 100 μL of the culture solution subjected to shaking culture at 200 rpm and 37° C. for 16 hours was transplanted into 10 mL of TB liquid medium, and after shaking culture at 200 rpm and 30° C. for 24 hours, 10 μL of isopropyl-β-D-galactopyranoside (IPTG) was added to induce gene expression, and further the culture was continued for 48 hours. Chloramphenicol (30 mg/L) and kanamycin (40 mg/L) as antibiotics were added to the medium.

A volume of 1 mL of the obtained culture solution was centrifuged at 8,000 g for 1 minute, and the supernatant was removed to collect a cell fraction. The cell fraction was suspended in 1% sodium chloride solution and centrifuged at 8,000 g for 1 minute, the supernatant was removed, and the cells were collected. Acetone/methanol (7:3 (volume basis)) were added to the recovered cells to extract the carotenoid, centrifuged at 12,000 g for 2 minutes, and the supernatant was used for carotenoid analysis.

The obtained supernatant was subjected to separation of carotenoids using HPLC Chromaster system manufactured by Hitachi, Ltd. Using Inertsil ODS-3 (4.6×150 mm, 5 μm, GL Sciences) as a column, acetonitrile as a mobile phase A, and isopropanol as a mobile phase B, the mobile phase A and the mobile phase B were fed at the ratio of 100:0 for 5 minutes, and then the mobile phase A and the mobile phase B were fed by gradient for 5 minutes such that the ratio of the mobile phaseA:the mobile phase B was changed from 100:0 to 50:50 (volume basis), and the ratio of 50:50 was further held for 5 minutes.

As a result, as shown in the results of Comparative Example 2-1 and Comparative Example 2-2 in FIG. 4, when either CaCCS or L1CCS were co-expressed, there was no change in the produced carotenoid, and production of capsanthin could not be confirmed.

Example 1

Figure 5:
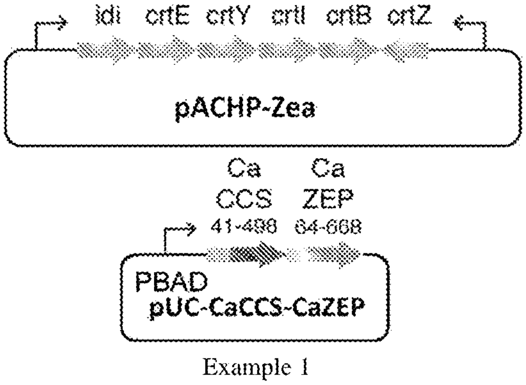
FIG. 5 is a schematic diagram of a recombinant vector produced in Example 1.

In this example, pACHP-Zea shown in FIG. 5 was constructed as the first recombinant vector to be incorporated, and pUC-CaCCS-CaZEP shown in FIG. 5 was constructed as the second recombinant vector. These recombinant vectors were designed such that the expression level of upstream gene was relatively low due to the promoter unique to the carotenoid biosynthesis gene (derived from *Pantoea ananatis*), and the expression level of downstream gene was relatively high due to PBAD. An outline of the first recombinant vector and the second recombinant vector of this example is shown in Table 3.

TABLE 3

| | Recombinant vector | Promoter | Promoter relative intensity | Vector constitution (abbreviation) |
|---|---|---|---|---|
| Example 1 | First | Derived from *pantoea ananatis* | Low | pACHP-Zea |
| | Second | PBAD | High | pUC-CaCCS$^{(*2)}$-CaZEP$^{(*1)}$ (*2: $CaCCS_{41-498}$)(*1: $CaZEP_{64-668}$) |

pACHP-Zea as the first recombinant vector was prepared in the same manner as in Comparative Example 1. According to the report of Non-Patent Document 3, regarding this pACHP-Zea, it has been found that β-carotene is not detected in the carotenoid composition with the transformant, and zeaxanthin occupies the total carotenoid.

pUC-CaCCS-CaZEP as the second recombinant vector was generated by placing $CaZEP_{64-668}$ and $CaCCS_{41-498}$ downstream of the PBAD promoter of the pUC vector.

Both the first recombinant vector and the second recombinant vector were introduced into *E. coli* JM101 (DE3) in the same manner as in Comparative Example 1.

After introduction of the recombinant vector, a single colony on the LB medium was transplanted into 3 mL of LB liquid medium, and cultured with shaking at 200 rpm at 37° C. for 16 hours. A volume of 100 μL of the culture medium was transplanted into 10 mL of TB liquid medium, and after 24 hours of shaking culture at 200 rpm at 30° C., 10 μL of isopropyl-β-D-galactopyranoside (IPTG) was added to induce gene expression, and the culture was continued for 48 hours. Chloramphenicol (30 mg/L) and kanamycin (40 mg/L) as antibiotics were added to the medium.

A volume of 1 mL of the obtained culture solution was centrifuged at 8,000 g for 1 minute, and the supernatant was removed to collect a cell fraction. The cell fraction was suspended in 1% sodium chloride solution and centrifuged at 8,000 g for 1 minute, the supernatant was removed, and the cells were collected. Acetone/methanol (7:3 by volume) were added to extract the carotenoid, centrifuged at 12,000 g for 2 minutes and the supernatant was used for carotenoid analysis.

The obtained supernatant was subjected to separation of carotenoids using HPLC Chromaster system manufactured by Hitachi, Ltd. Using Inertsil ODS-3 (4.6×150 mm, 5 μm, GL Sciences) as a column, acetonitrile as a mobile phase A, and isopropanol as a mobile phase B, the mobile phase A and the mobile phase B were fed at the ratio of 100:0 for 5 minutes, and then the mobile phase A and the mobile phase B were fed by gradient for 5 minutes such that the ratio of the mobile phaseA:the mobile phase B was changed from 100:0 to 50:50 (volume basis), and the ratio of 50:50 was further held for 5 minutes to separate carotenoids.

The obtained supernatant (carotenoid) was also subjected to Aquity H-class UPLC (Waters). Using Aquity UPLC BEH C18 column (2.1×100 mm, 1.7 μm, Waters) as a column, acetonitrile:ultrapure water (85:15 (volume ratio)) as a mobile phase A, and acetonitrile:methanol (65:35 (volume ratio)) as a mobile phase B, the mobile phase A and mobile phase C were fed by gradient for 8 minutes such that the ratio of A:B was changed from 100:0 to 0:100, and then the carotenoid was separated by a program of holding at the ratio of 0:100 for 5 minutes.

Figure 6:
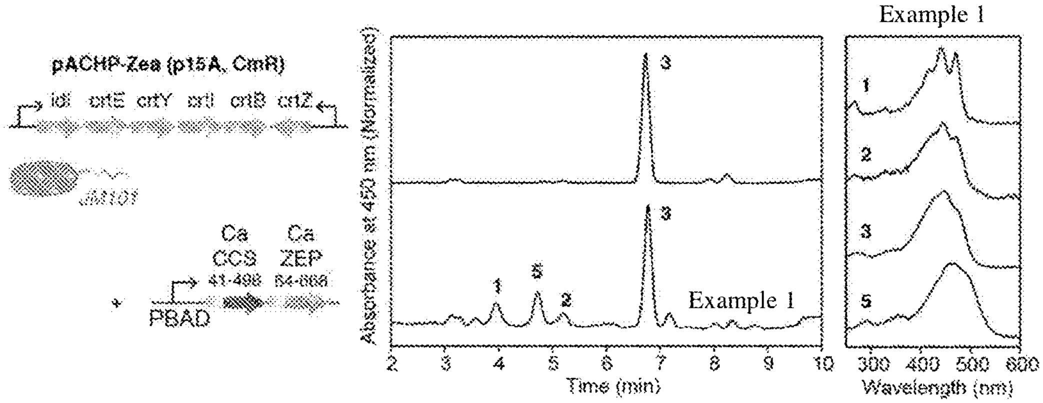
FIG. 6 shows an HPLC chromatogram of a carotenoid composition obtained in Example 1.
Figure 6:
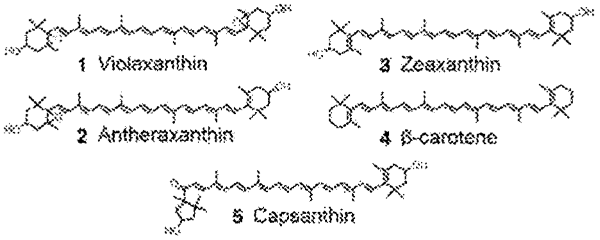

The results are shown in FIG. 6. FIG. 6 shows the results of the HPLC chromatogram when the first expression vector is expressed alone (upper part) and the HPLC chromatogram when the first expression vector and the second expression vector are co-expressed (Example 1) (lower part), and the absorption spectra of peaks 1, 2, 3, and 5 detected in the latter (Example 1). As shown in FIG. 6, a new peak 5 could be confirmed by the co-expression of the first expression vector and the second expression vector.

Figure 7:
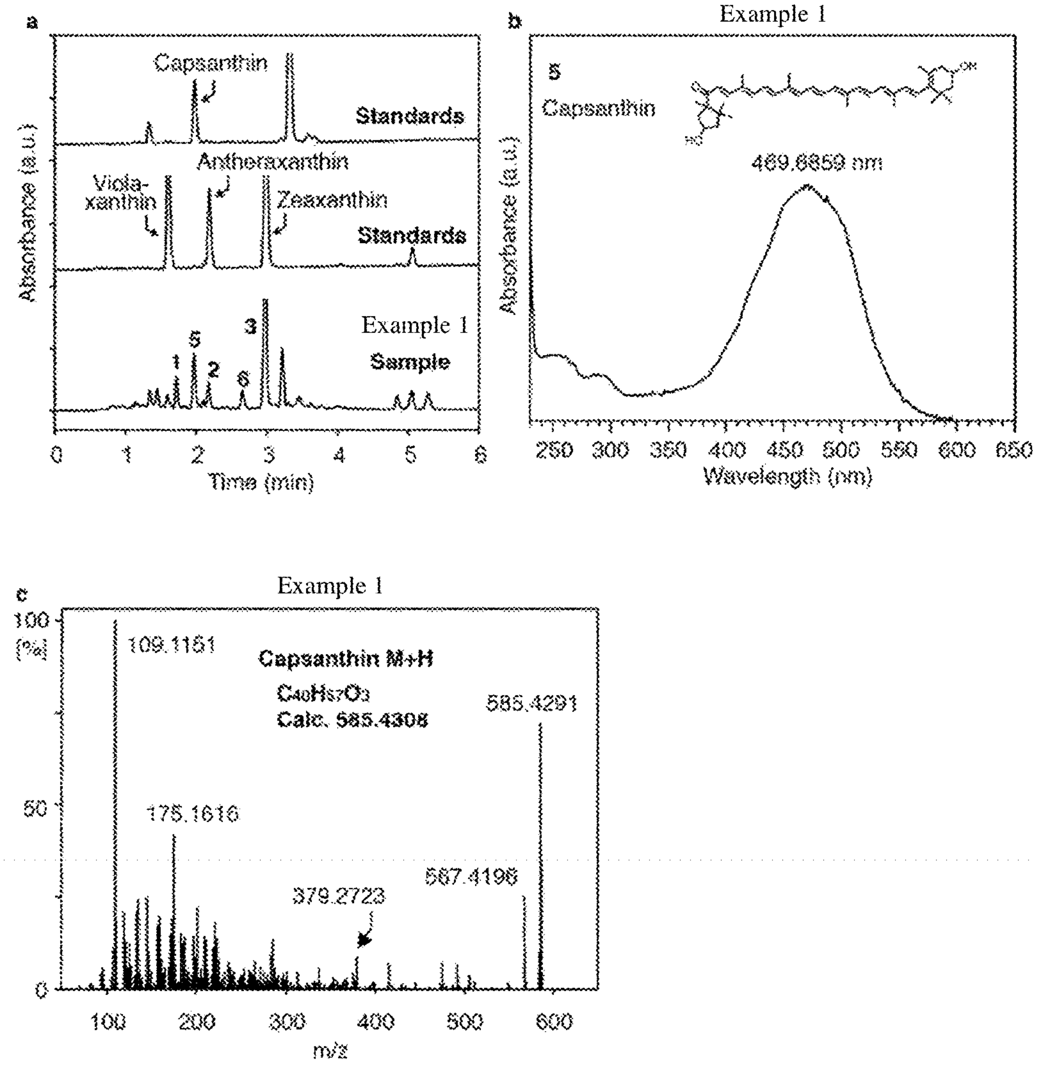
FIG. 7 shows a UPLC chromatogram (a) of a carotenoid composition obtained in Example 1, an absorption spectrum (b) of capsanthin, and a mass spectrum (c) of capsanthin.

The same supernatant (carotenoid)(sample) was analyzed with UPLC and the results compared to standards are shown in FIG. 7*a*. As shown in FIG. 7*a*, a new peak 5 could be confirmed by co-expression of the first expression vector and the second expression vector (Example 1). The absorption spectrum of the peak 5 is shown in FIG. 7*b*. The peak 5 confirmed in the UPLC chromatogram of FIG. 7*a* showed a retention time and absorption spectrum similar to those of capsanthin. As a result of calculation based on the molar absorption coefficient from the peak intensity, the production amount of capsanthin per culture solution was 292 μg/L.

LC/MS analysis of the peak 5 was performed using a Waters Xevo G2S Q TOF mass spectrometer (Waters) equipped with the Acquity UPLC system. As analysis conditions with a time-of-flight mass spectrometer (ESI-TOF-MS), a nitrogen gas was used at a capillary voltage of 3.2 kV, a cone voltage of 20 eV, 120° C., and 30 L/h, and m/z of 100 to 1,500 was scanned. MS/MS spectra were measured on a quadrupole TOF MS/MS instrument using argon at a collision energy of 20 V. UV-VIS absorption spectra were recorded between 200 nm and 600 nm using a photodiode array. HPLC separation used Acquity 1.7 μm BEH UPLC C18 column (Waters) with a gradient program of acetonitrile:ultrapure water (85:15 by volume) to acetonitrile: methanol (65:35 by volume) (flow rate 0.4 mL/min, 15 minutes). The results are shown in FIG. 7*c*. The molecular ion peak shown in FIG. 7*c* coincided with the calculated value of the molecular weight of capsanthin.

The $^1H$ NMR (500 MHz) spectrum of the peak 5 was measured using a Varian UNITY INOVA 500 spectrometer (Varian Corporation) using TMS as an internal standard and using deuterated chloroform. As a result, the peak 5 was identified as capsanthin.

Example 2 (Example 2-1 and Example 2-2)

Figure 8:
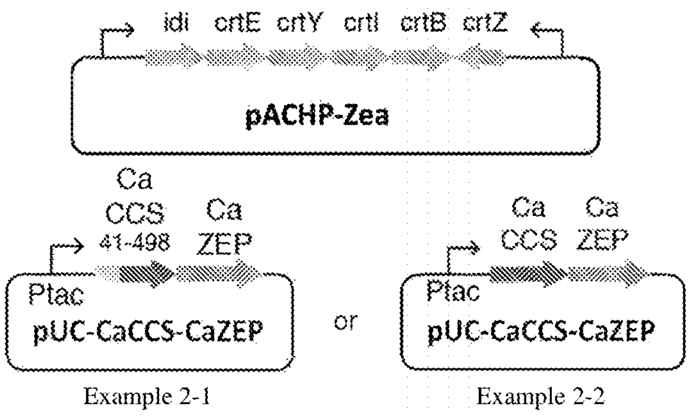
FIG. 8 is a schematic diagram of recombinant vectors produced in Example 2 (Example 2-1 and Example 2-2).

In this example, pACHP-Zea shown in FIG. 8 was constructed as the first recombinant vector to be incorporated, and pUC-CaCCS-CaZEP (two kinds) shown in FIG. 8 was constructed as the second recombinant vector. These recombinant vectors were designed so that the expression level of the upstream gene was relatively low by the promoter unique to the carotenoid biosynthesis gene (derived from *Pantoea ananatis*), and the expression level of the downstream gene was relatively high by Ptac. An outline of the first recombinant vector and the second recombinant vector of this example is shown in Table 4.

TABLE 4

| | Recombinant vector | Promoter | Promoter relative intensity | Vector constitution (abbreviation) |
|---|---|---|---|---|
| Example 2-1 | First | Derived from *Pantoea ananatis* | Low | pACHP-Zea |
| | Second | Ptac | High | pUC-CaCCS$^{(*2)}$-CaZEP (*2: CaCCS$_{41-498}$) |
| Example 2-2 | First | Derived from *Pantoea ananatis* | Low | pACHP-Zea |
| | Second | Ptac | High | pUC-CaCCS-CaZEP |

pACHP-Zea as the first recombinant vector was prepared in the same manner as in Comparative Example 1. According to the report of Non-Patent Document 3, regarding this pACHP-Zea, it has been found that β-carotene is not detected in the carotenoid composition with the transformant, and zeaxanthin occupies the total carotenoid.

The pUC-CaCCS-CaZEP as the second recombinant vector was produced by placing CaZEP (signal sequence not removed) and CaCCS (signal sequence not removed) or CaCCS$_{41-498}$ downstream of the Ptac promoter of the pUC vector.

Both the first recombinant vector and the second recombinant vector were introduced into *E. coli* JM101 (DE3) in the same manner as in Comparative Example 1.

After introduction of the recombinant vector, a single colony on the LB medium was transplanted into 0.5 mL of LB liquid medium, and cultured with shaking at 1,000 rpm at 37° C. for 16 hours. A volume of 20 μL of the culture medium was transplanted into 2 mL of TB liquid medium, and after shaking culture at 1,000 rpm at 30° C. for 24 hours, 2 μL of 1 M isopropyl-β-D-galactopyranoside (IPTG) was added to induce gene expression. The cells were further cultured for 48 hours. As antibiotics, chloramphenicol (30 mg/L) and kanamycin (40 mg/L) were added to the medium.

A volume of 1 mL of the obtained culture solution was centrifuged at 8,000 g for 1 minute, and the supernatant was removed to collect a cell fraction. The cell fraction was suspended in 1% sodium chloride solution and centrifuged at 8,000 g for 1 minute, the supernatant was removed, and the cells were collected. Acetone/methanol (7:3 by volume) were added to extract the carotenoid, centrifuged at 12,000 g for 2 minutes and the supernatant was used for carotenoid analysis.

The obtained supernatant was subjected to separation of carotenoids using HPLC Chromaster system manufactured by Hitachi, Ltd. Using Inertsil ODS-3 (4.6×150 mm, 5 μm, GL Sciences) as a column, acetonitrile as a mobile phase A, and isopropanol as a mobile phase B, the mobile phase A and the mobile phase B were fed at the ratio of 100:0 for 5 minutes, and then the mobile phase A and the mobile phase B were fed by gradient for 5 minutes such that the ratio of the mobile phaseA:the mobile phase B was changed from 100:0 to 50:50 (volume basis), and the ratio of 50:50 was further held for 5 minutes to separate carotenoids.

For comparison, the same operation was performed using a second expression vector for comparison produced in the same manner except that neither CaCCS nor CaCCS$_{41-498}$ was incorporated into the second expression vector described above.

Figure 9:
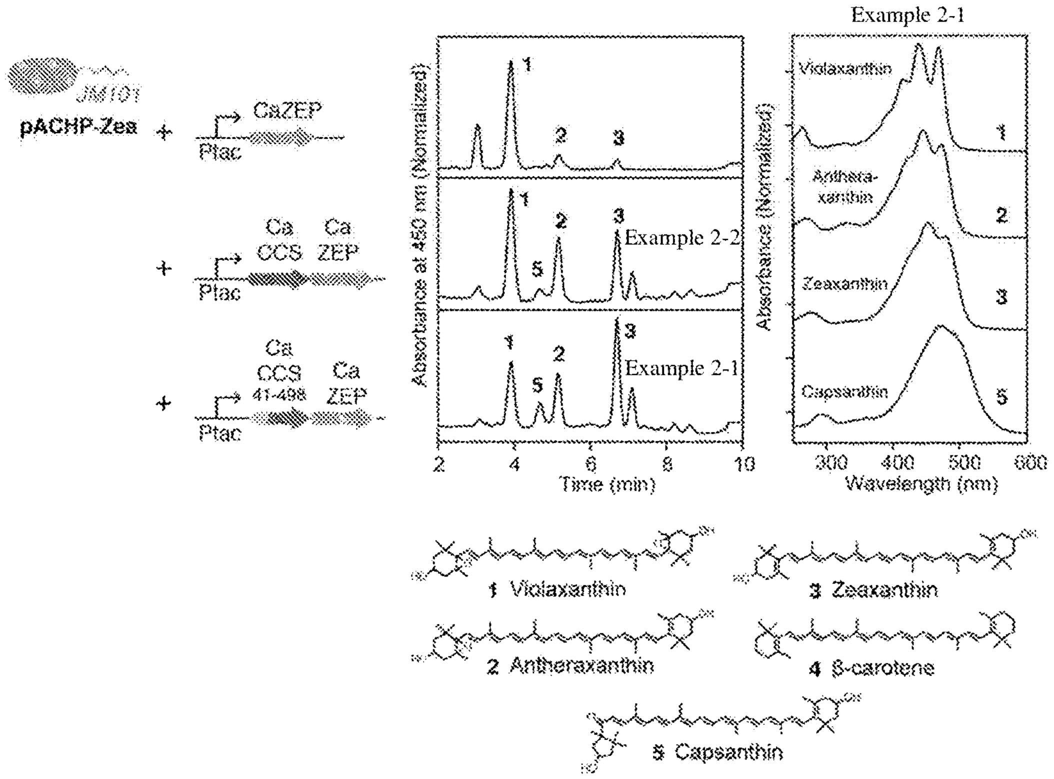
FIG. 9 shows an HPLC chromatogram of carotenoid compositions obtained in Example 2 (Example 2-1 and Example 2-2).

The analysis results are shown in FIG. 9. FIG. 9 shows the results of an HPLC chromatogram in the case of co-expressing the first expression vector and the second expression vector for comparison (upper part), an HPLC chromatogram in the case of co-expressing the first expression vector and the second expression vector (one incorporating full-length CaCCS: Example 2-2) (middle part), and an HPLC chromatogram in the case of co-expressing the first expression vector and the second expression vector (one incorporating CaCCS$_{41-498}$ with a signal sequence removed: Example 2-1) (lower part), and absorption spectra of peaks 1, 2, 3, and 5 detected in the case of co-expressing the first expression vector and the second expression vector (one incorporating CaCCS$_{41-498}$ with a signal sequence removed: Example 2-1). As shown in FIG. 9, a new peak 5, that is, capsanthin could be confirmed by co-expression of the first expression vector and the second expression vector.

Figure 10:
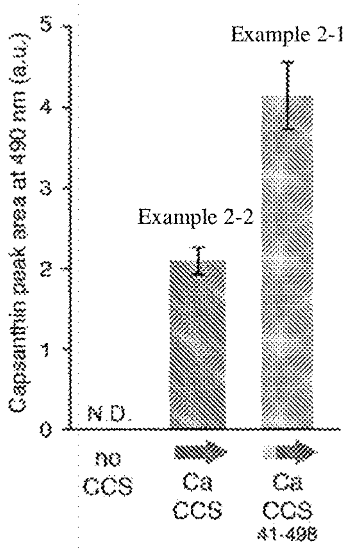
FIG. 10 shows the production amount of capsanthin in carotenoid compositions obtained in Example 2 (Example 2-1 and Example 2-2).

In addition, FIG. 10 shows a graph comparing the intensities of the peaks 5 of capsanthin in FIG. 9. As shown in FIG. 10, capsanthin was produced more in the case of using the second expression vector incorporating CCS$_{41-498}$ from which the signal sequence was removed (Example 2-1) than in the case of using the second expression vector incorporating the full-length CCS (Example 2-2).

Furthermore, as a result of calculating the production amount of capsanthin of the peak 5 from the peak intensity based on the molar absorption coefficient, the production amount of capsanthin per culture medium in the case of using the second expression vector incorporating the full-length CCS (Example 2-2) was 326 μg/L, and the production amount of capsanthin per culture medium in the case of using the second expression vector incorporating CCS$_{41-498}$ from which the signal sequence has been removed (Example 2-1) was 452 μg/L.

Example 3 (Example 3-1, Example 3-2, Example 3-3)

In this example, the same pACHP-Zea as in Comparative Example 1 was used as the first recombinant vector. According to the report of Non-Patent Document 3, regarding this pACHP-Zea, it has been found that β-carotene is not detected in the carotenoid composition with the transformant, and zeaxanthin occupies the total carotenoid.

Figure 11:
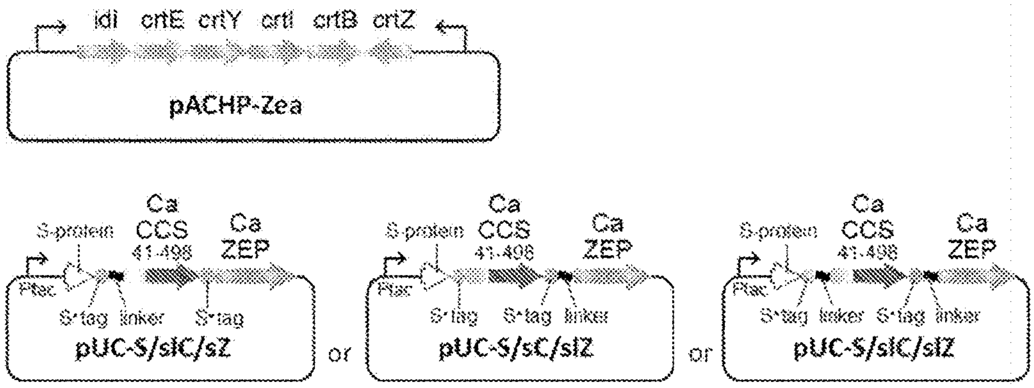
FIG. 11 is a schematic diagram of recombinant vectors produced in Example 3 (Example 3-1 to Example 3-3).

As the second recombinant vector, pUC-S/slC/sZ, pUC-S/sC/slZ, or pUC-S/slC/slZ ("S" represents S Protein, "s" represents S-Tag, and "l" represents a linker) shown in FIG. 11 was produced. An outline of the first recombinant vector and the second recombinant vector of this example is shown in Table 5.

TABLE 5

| | Recombinant vector | Promoter | Promoter relative intensity | Vector constitution (For the second recombinant vector, the upper row shows the abbreviations and the lower row shows the detailed structure) |
|---|---|---|---|---|
| Example 3-1 | First | Derived from *Pantoea ananatis* | Low | pACHP-Zea |
| | Second | Ptac | High | pUC-S/slC/sZ<br>S protein/s tag + linker + $CaCCS_{41-498}$/s tag + CaZEP |
| Example 3-2 | First | Derived from *Pantoea ananatis* | Low | pACHP-Zea |
| | Second | Ptac | High | S/sC/slZ<br>S protein/s tag + $CaCCS_{41-498}$/s tag + linker + CaZEP |
| Example 3-3 | First | Derived from *Pantoea ananatis* | Low | pACHP-Zea |
| | Second | Ptac | High | S/slC/slZ<br>S protein/s tag + linker + $CaCCS_{41-498}$/s tag + linker + CaZEP |

As schematically shown in FIG. 12, this second recombinant vector was designed so that CCS and ZEP were expressed as proteins fused with S-Tag (In FIG. 12, illustrated as "S tag+linker+CCS" and "S tag+linker+ZEP"), respectively, and then indirectly bound via multimerized S Protein (In FIG. 12, it is indicated as "multimer") to form a complex (In FIG. 12, it is indicated as "complex"). An aspect of the second recombinant vector designed as described above is also referred to as "S-Tag incorporated".

The three second recombinant vectors of pUC-S/slC/sZ, pUC-S/sC/slZ, and pUC-S/slC/slZ shown in FIG. 11 were designed so that the combination of the presence or absence of a linker between S-Tag and CCS and/or between S-Tag and ZEP was different. By making the introduction position of the linker in the second recombinant vector into which S-Tag was incorporated different in this way, three conditions in which the degree of freedom between CCS and ZEP was different after expression were constructed.

Sequence information on construction of the second recombinant vector into which S-Tag is incorporated is shown in Table 6 below.

TABLE 6

| | Base sequence | Amino acid sequence |
|---|---|---|
| S protein | SEQ ID NO: 1 | SEQ ID NO: 2 |
| S-Tag | SEQ ID NO: 3 | SEQ ID NO: 4 |
| S-Tag/CaCCS | SEQ ID NO: 5 | SEQ ID NO: 6 |
| S-Tag/linker/CaCCS | SEQ ID NO: 7 | SEQ ID NO: 8 |
| S-Tag/CaZEP | SEQ ID NO: 9 | SEQ ID NO: 10 |
| S-Tag/linker/CaZEP | SEQ ID NO: 11 | SEQ ID NO: 12 |

As shown in SEQ ID NOs: 8 and 12, a linker consisting of 20 amino acid residues ($\{GS\}_{10}$ linker) in which 10 units of a unit (GS) consisting of glycine (G) of a nonpolar amino acid and serine (S) of a polar amino acid were continuous was used as the linker. The fusion position of S-Tag was the N-terminus of each of CaCCS and CaZEP. As a construct into which S protein, S-Tag, or the like is introduced, pUClac-ptac-CaCCSM40-CaZEP (pMF541) (Furubayashi, M., Kubo, A., Takemura, M., Otani, Y., Maoka, T., Terada, Y., Yaoi, K., Ohdan, K., Misawa, N. and Mitani, Y. (2021) J. Agric. Food Chem., 69, 5076-5085) was used.

The first recombinant vector and the second recombinant vector were introduced in the same manner as in Example 1, then a single colony on the LB medium was transplanted into 3 mL of a 2YT liquid medium, and cultured with shaking at 105 rpm and 28° C. for 16 hours using Shaking Bath BW201 manufactured by Yamato Scientific Co., Ltd. A volume of 20 μL of the culture solution was transplanted into 2.1 mL of TB liquid medium, and after shaking culture was performed at 180 rpm and 30° C. for 4 hours using Lab-Therm LT-X manufactured by Kuhner, 0.1 mM isopropyl-β-D-galactopyranoside (IPTG) was added to induce gene expression, and the culture was continued for 48 hours. As antibiotics, chloramphenicol (30 mg/L) and ampicillin (100 mg/L) were added to the medium.

A volume of 1 mL of the obtained culture solution was centrifuged at 8,000 g for 1 minute, and the supernatant was removed to collect a cell fraction. The cell fraction was suspended in 1% sodium chloride solution and centrifuged at 8,000 g for 1 minute, the supernatant was removed, and the cells were collected. Methanol and chloroform were added to extract the carotenoid, centrifuged at 12,000 g for 2 minutes, and the supernatant was used for carotenoid analysis.

The obtained supernatant was subjected to separation of carotenoids using HPLC Chromaster system manufactured by Hitachi, Ltd. Using Inertsil ODS-3 (4.6×150 mm, 5 μm, GL Sciences) as a column, acetonitrile as a mobile phase A, and isopropanol as a mobile phase B, the mobile phase A and the mobile phase B were fed at the ratio of 100:0 for 5 minutes, and then the mobile phase A and the mobile phase B were fed by gradient for 5 minutes such that the ratio of the mobile phaseA:the mobile phase B was changed from 100:0 to 50:50 (volume basis), and the ratio of 50:50 was further held for 5 minutes to separate carotenoids.

Figure 13:
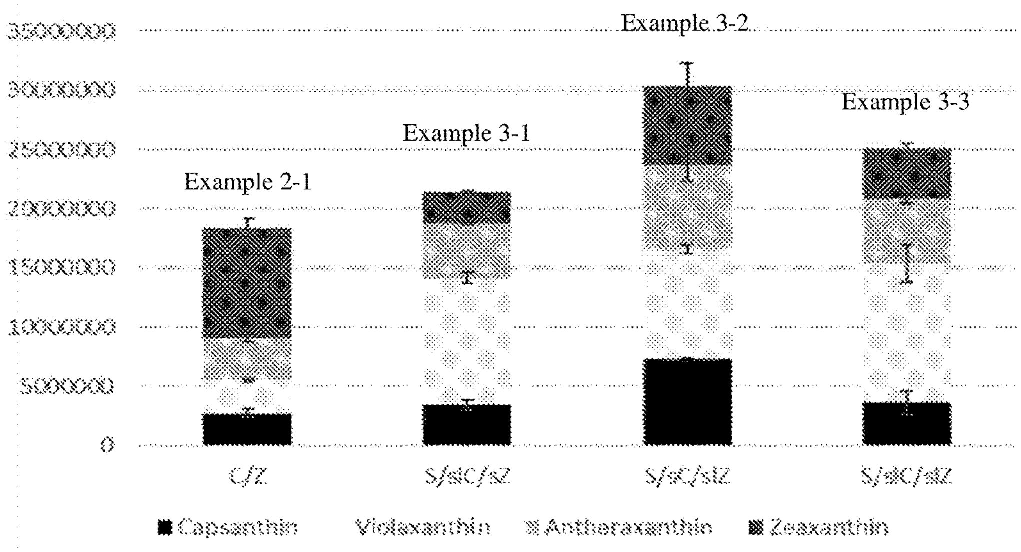
FIG. 13 shows the analysis results of carotenoid compositions obtained in Example 3 (Example 3-1 to Example 3-3).

A graph comparing the peak intensities of the carotenoids in the HPLC analysis is shown in FIG. 13. In x FIG. 13, results in the case of using the second recombinant vector pUC-$CaCCS_{41-498}$-CaZEP (in the figure, it is indicated as "C/Z") used in Example 2-1 in which S-Tag is not incorporated are also shown together. As shown in FIG. 13, more capsanthin was accumulated in the case of using the second recombinant vector into which S-Tag was incorporated (Example 3-1 to Example 3-3) than in the case where S-Tag was not incorporated (Example 2-1). In addition, among the three types of second recombinant vectors in which S-Tag was incorporated, when pUC-S/sC/slZ in which a linker was incorporated between S-Tag and ZEP was used (Example 3-2), the accumulation amount of capsanthin was remarkably large.

Further, the results calculated from the peak intensity based on the molar absorption coefficient are shown in Table 7. The production amount of capsanthin per culture medium in the case of using the second recombinant vector into which the S-Tag was incorporated (Examples 3-1 to 3-3) was improved as compared with the production amount of capsanthin per culture medium in the case of using the second recombinant vector into which the S-tag was not incorporated (Example 2-1). In particular, when pUC-S/sC/slZ in which a linker was incorporated between S-Tag and ZEP was used as the second recombinant vector (Example 3-2), not only the production amount of capsanthin per culture solution was remarkably improved, but also the ratio of capsanthin to the total amount of carotenoids shown in Table 7 was remarkably improved.

TABLE 7

| | Example 2-2 C/Z | | Example 3-1 S/slC/sZ | | Example 3-2 S/sC/slZ | | Example 3-3 S/slC/slZ | |
|---|---|---|---|---|---|---|---|---|
| | ug/gFW | ug/L | ug/gFW | ug/L | ug/gFW | ug/L | ug/gFW | ug/L |
| Zeaxanthin | 3.88 | 1151.7 | 1.58 | 334.44 | 3.57 | 817.68 | 2.53 | 522.86 |
| Antheraxanthin | 1.48 | 440.41 | 2.72 | 574.75 | 3.91 | 894.03 | 3.35 | 692.94 |
| Violaxanthin | 0.98 | 289.22 | 5.28 | 1113.7 | 4.27 | 977.97 | 5.93 | 1225.5 |
| Capsanthin | 1.16 | 343.41 | 2.04 | 431.13 | 3.94 | 901.4 | 2.19 | 452.13 |
| Total | 7.5 | 2224.7 | 11.62 | 2454.1 | 15.7 | 3591.1 | 14 | 2893.4 |
| Capsanthin/ Total (%) | 15.5 | | 17.6 | | 25.1 | | 15.6 | |

Figure 14:
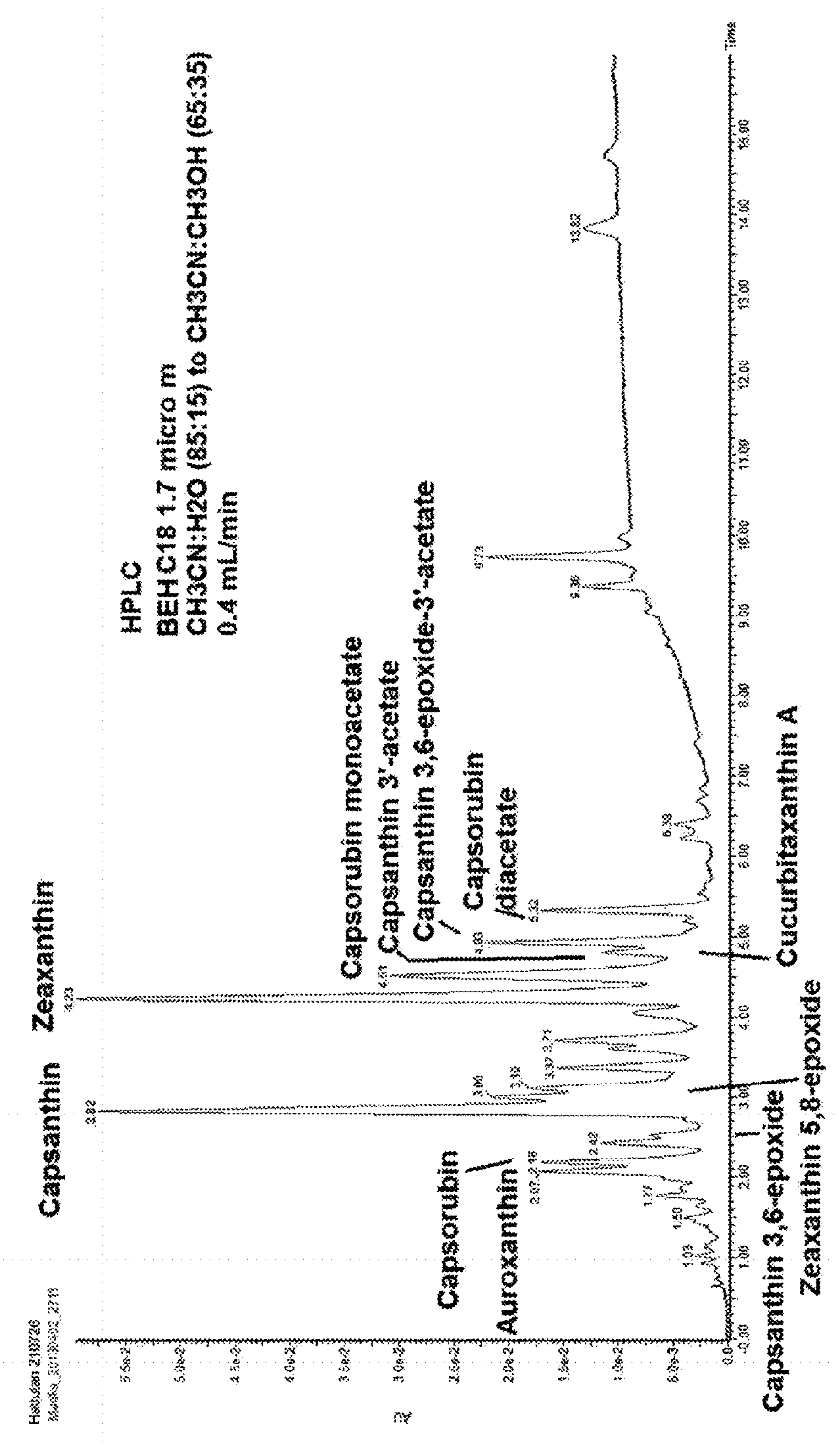
FIG. 14 shows the analysis results of a carotenoid composition obtained in Example 3 (Example 3-2).

In addition, FIG. 14 shows the results of UPLC analysis in the same manner as in Example 1 of the carotenoids obtained when pUC-S/sC/slZ was used as the second vector (Example 3-2). As is clear from FIG. 14, the respective peaks of capsanthin 3'-acetate, capsanthin 3,6-epoxide, capsanthin 3,6-epoxide 3'-acetate, capsorubin 3-acetate, capsorubin diacetate, and cucurbitaxanthin A were detected. As a result of LC/MS analysis of these carotenoids in the same manner as in Example 1, the molecular ion peak coincided with the calculated value of the molecular weight of each carotenoid. Furthermore, the results of calculating the ratio of each carotenoid from the peak intensity of the UPLC analysis are shown in Table 8.

TABLE 8

| Carotenoids | % |
|---|---|
| β-Carotene | 3.3 |
| β-Cryptoxanthin | 3.7 |
| Capsorubin diacetate | 4.1 |
| Capsanthin 3,6-epoxide-3'-acetate | 5.5 |
| Cucurbitaxanthin A | 2.8 |
| Capsanthin 3'-acetate | 3.5 |
| Capsorubin monoacetate | 12.1 |
| Zeaxanthin | 19.4 |

TABLE 8-continued

| Carotenoids | % |
|---|---|
| Zeaxanthin epoxide | 9.4 |
| Capsanthin | 18.5 |
| Capsanthin 3,6-epoxide | 3.2 |
| Capsorubin | 3.7 |
| Auroxanthin | 3.8 |
| Others | 7.0 |
| | 100.0 |

For NMR measurement of the carotenoid, silica gel chromatography was used, and the polarity was sequentially increased from hexane to ether:hexane (1:1), and ether: acetone (1:1), each fraction was fractionated and concentrated, then further, a silica gel (Cosmosil 5 SL-II) column 10×250 mm was used, acetone:hexane (3:7) was used as a mobile phase, and separated at a flow rate of 2 ml/min to obtain a sample from which each carotenoid peak had been fractionated, and the sample was used for E NMR measurement in the same manner as in Example 1. The structural formulae of the carotenoids (capsanthin, capsorubin, cucurbitaxanthin A, other derivatives, etc.) identified as a result of $^1$H NMR analysis are shown in the following formulae.

[Chemical Formula 1]

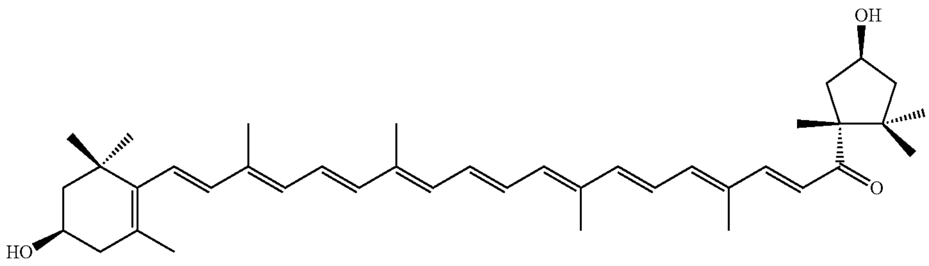

Capsanthin

-continued
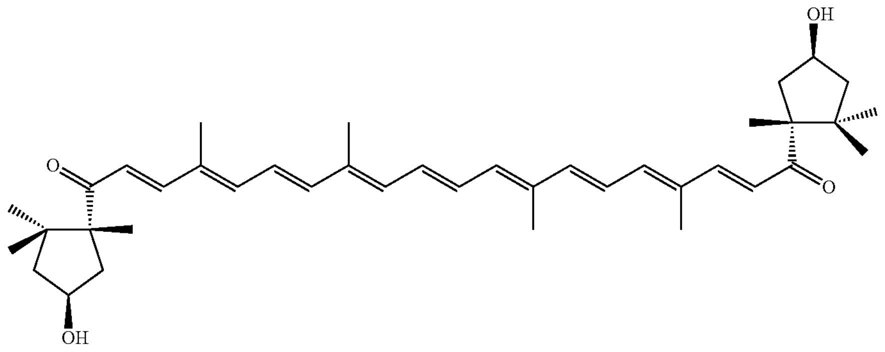
Capsorubin
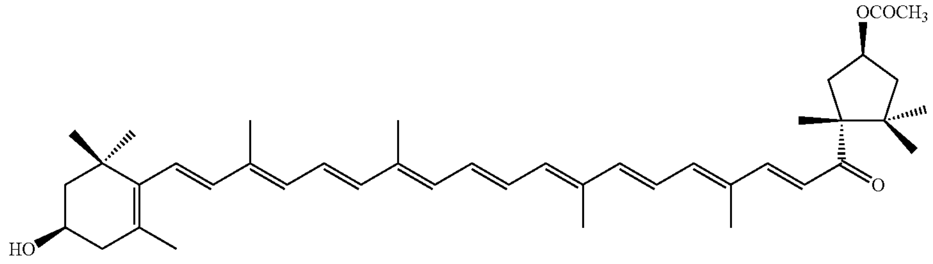
Capsanthin 3′-acetate
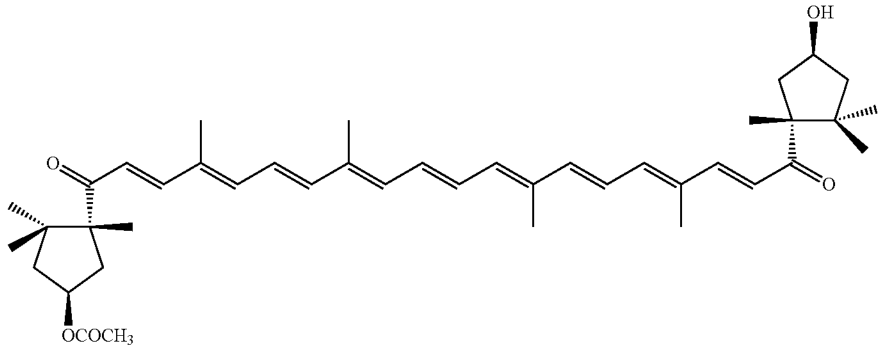
Capsorubin 3-acetate
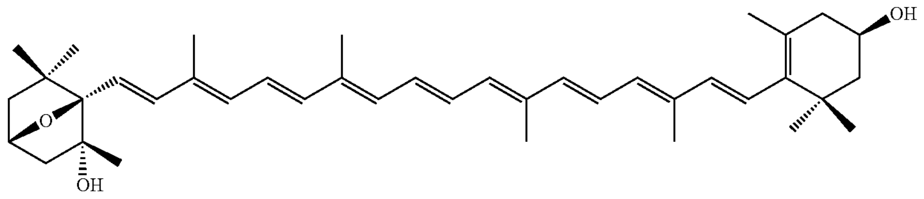
Cucurbitaxanthin A
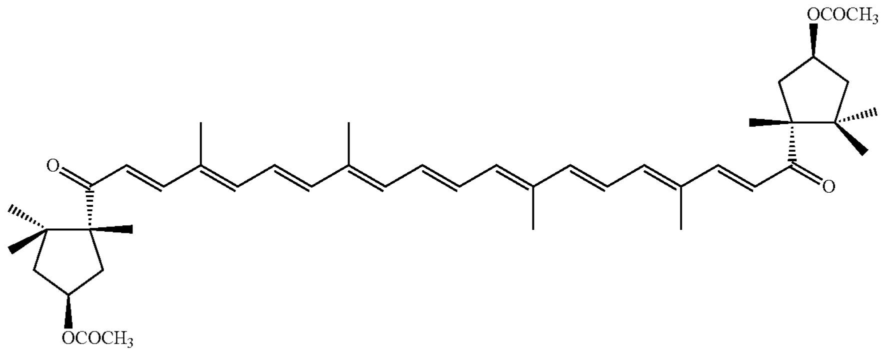
Capsorubin diacetate -continued

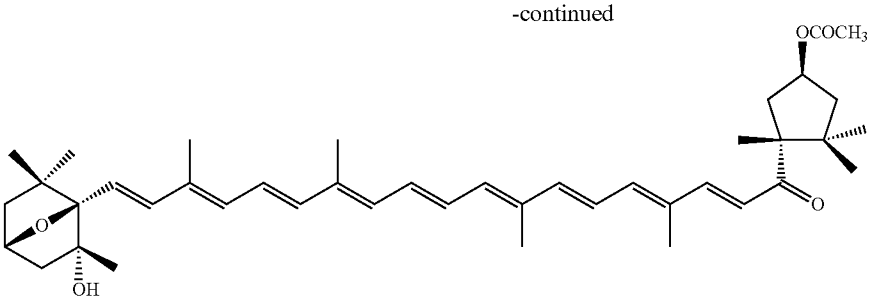

Capsanthin 3,6-epoxide

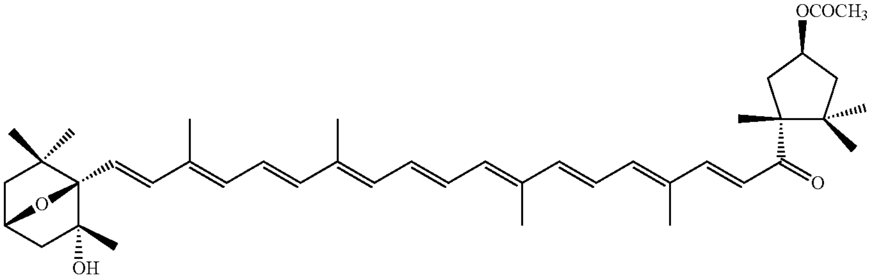

Capsanthin 3,6-epoxide 3′-acetate

SEQUENCE LISTING FREE TEXT

SEQ ID NO: 3 is obtained by substituting the 34th to 36th positions of the base sequence encoding S-Tag with the sequence encoding phenylalanine.

SEQ ID NO: 4 is one in which the 12th position in the amino acid sequence of S-Tag is substituted with phenylalanine.

SEQ ID NOs: 5 and 6 represent the base sequence and amino acid sequence of CaCCS into which S-Tag has been introduced, respectively.

SEQ ID NOs: 7 and 8 represent the base sequence and amino acid sequence of CaCCS into which S-Tag has been introduced via a linker, respectively.

SEQ ID NOs: 9 and 10 represent the base sequence and amino acid sequence of CaZEP into which S-Tag has been introduced, respectively.

SEQ ID NOs: 11 and 12 represent the base sequence and amino acid sequence of CaZEP into which S-Tag has been introduced via a linker, respectively.

The invention claimed is:

1. A transformant in which:

a first promoter, and an upstream gene of a carotenoid biosynthesis gene including a crtI gene, a crtB gene, a crtE gene, a crtY gene and a crtZ gene operably linked to the first promoter, and a second promoter having higher promoter intensity than that of the first promoter, and a ZEP gene and a CCS gene operably linked to the second promoter, have been introduced into a host cell.

2. The transformant according to claim 1, wherein a difference in promoter intensity between the first promoter and the second promoter is equal to or greater than a difference in promoter intensity between the promoter unique to the carotenoid biosynthesis gene and PBAD.

3. The transformant according to claim 1, wherein the first promoter is Plac or a promoter unique to a carotenoid biosynthesis gene.

4. The transformant according to claim 1, wherein the second promoter is PBAD or Ptac.

5. The transformant according to claim 1, further comprising:

an S protein gene, an S tag gene, and a linker gene introduced into the host cell, wherein the S-tag gene is linked to each of the ZEP gene and the CCS gene, and wherein the linker gene is interposed and linked between the ZEP gene and the S-tag gene and/or between the CCS gene and the S-tag gene.

6. The transformant according to claim 5, wherein the S-tag encoded by the S-tag gene is any one of the following polypeptides (1) and (2):

(1) a polypeptide comprising the amino acid sequence set forth in SEQ ID NO: 4;

(2) a polypeptide that has at least 90% identity to SEQ ID NO: 4, wherein the amino acid at position 12 is Phe and wherein the polypeptide specifically binds to S protein.

7. The transformant according to claim 5, wherein the linker gene is interposed and linked at least between the ZEP gene and the S-tag gene.

8. The transformant according to claim 5, wherein the linker gene is interposed and linked between the ZEP gene and the S-tag gene, and is not interposed between the CCS gene and the S-tag gene.

9. The transformant according to claim 1, wherein the host cell is a bacterial host cell.

10. The transformant according to claim 9, wherein the bacterial host cell is an *E. coli* host cell.

11. A production method for a carotenoid composition, comprising a step of culturing the transformant according to claim 1.

12. The production method according to claim 11, wherein the carotenoid composition comprises capsanthin.

13. The production method according to claim 11, wherein the carotenoid composition comprises capsorubin, capsanthin 3'-acetate, capsorubin 3-acetate, cucurbitaxanthin A, capsorubin diacetate, capsanthin 3,6-epoxide, and/or capsanthin 3,6-epoxide 3'-acetate.

* * * * *